(12) United States Patent
Yang et al.

(10) Patent No.: US 11,542,314 B2
(45) Date of Patent: Jan. 3, 2023

(54) STEP-FUNCTION CHANNELRHODOPSINS FOR OPTICAL CONTROL OF CELLS

(71) Applicant: Massachusetts Institute of Technology, Cambridge, MA (US)

(72) Inventors: Aimei Yang, Natick, MA (US); Demian Park, Cambridge, MA (US); Edward S. Boyden, Chestnut Hill, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 387 days.

(21) Appl. No.: 16/126,384

(22) Filed: Sep. 10, 2018

(65) Prior Publication Data

US 2019/0079074 A1   Mar. 14, 2019

Related U.S. Application Data

(60) Provisional application No. 62/556,616, filed on Sep. 11, 2017.

(51) Int. Cl.
| | | |
|---|---|---|
| *C07K 14/705* | (2006.01) | |
| *G01N 33/50* | (2006.01) | |
| *G01N 33/68* | (2006.01) | |
| *C07K 14/72* | (2006.01) | |
| *C12N 15/79* | (2006.01) | |

(52) U.S. Cl.
CPC .......... *C07K 14/705* (2013.01); *C07K 14/721* (2013.01); *G01N 33/502* (2013.01); *G01N 33/5076* (2013.01); *G01N 33/6872* (2013.01); *C07K 2319/00* (2013.01); *C12N 15/79* (2013.01); *G01N 2500/04* (2013.01)

(58) Field of Classification Search
None
See application file for complete search history.

(56) References Cited

U.S. PATENT DOCUMENTS

| 2010/0234273 A1 | 9/2010 | Boyden et al. |
| 2011/0165681 A1 | 7/2011 | Boyden et al. |

OTHER PUBLICATIONS

Klapoetke et al., "Independent optical excitation of distinct neural populations." Nature Methods, Mar. 2014, vol. 11, No. 3, 79 pages.
Chow et al., "High-Performance Genetically Targetable Optical Neural Silencing via Light-Driven Proton Pumps." Nature (2010), 463 (7277): 98-102.
Chow et al., "Chapter eighteen—Synthetic Physiology: Strategies for Adapting Tools from Nature for Genetically Target Control of Fast Biological Processes." Methods in Enzymology (2011) vol. 497, pp. 425-443.
Han et al., "Multiple-Color Optical Activation, Silencing, and Desynchronization of Neural Activity, with Single-Spike Temporal Resolution." PLOS One (2007).

*Primary Examiner* — Michael D Pak
(74) *Attorney, Agent, or Firm* — Pierce Atwood LLP

(57) ABSTRACT

The invention, in some aspects relates to light-activated ion channel molecules and methods for their use to alter cell activity and function. Light-activated ion channel molecules of the invention can be administered to subjects, expressed in cells, and activated with light, to alter membrane potential in the cells, and can be used in methods for assaying compounds, treating diseases and conditions, compound screening and more.

16 Claims, 3 Drawing Sheets
Specification includes a Sequence Listing.

STEP-FUNCTION CHANNELRHODOPSINS FOR OPTICAL CONTROL OF CELLS

RELATED APPLICATIONS

This application claims the benefit under 35 U.S.C. § 119(e) of U.S. Provisional application Ser. No. 62/556,616 filed Sep. 11, 2017, the disclosure of which is incorporated by reference herein in its entirety.

GOVERNMENT INTEREST

This invention was made with government support under grants 2-R01-DA029639-5, 1-R24-MH106075 and 1-R01-NS087950 from the National Institutes of Health. The government has certain rights in the invention.

FIELD OF THE INVENTION

The invention, in some aspects relates to compositions and methods for altering conductance across membranes, cell activity, and cell function, also relates to the use of exogenous light-activated ion channels in cells and subjects.

BACKGROUND OF THE INVENTION

Altering and controlling cell membrane and subcellular region ion permeability has permitted examination of characteristics of cells, tissues, and organisms. Light-driven pumps and channels have been used to silence or enhance cell activity. Molecular-genetic methods for preparing cells that can be activated (e.g., depolarized) or inactivated (e.g., hyperpolarized) by specific wavelengths of light have been developed (see, for example, Han, X. and E. S. Boyden, 2007, PLoS ONE 2, e299). Previously identified light-activated pumps and channels may be restricted to activation by particular wavelengths of light, localization, functional speed, etc. thus limiting their usefulness.

SUMMARY OF THE INVENTION

According to an aspect of the invention, light-activated ion channel polypeptides are provided that include an amino acid sequence set forth as SEQ ID NO: 1 or a functional variant thereof. In some embodiments, a functional variant of SEQ ID NO: 1 includes the amino acid sequence set forth as SEQ ID NO: 1 with 1, 2, 3, 4, or more amino acid sequence modifications, wherein a Serine (S) is present at the amino acid position that corresponds to amino acid 145 of SEQ ID NO: 1, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to amino acids 61-295 of SEQ ID NO: 1 and at least 95%, 96%, 97%, 98%, 99% or 100% sequence identity to the remaining amino acids in the sequence set forth as SEQ ID NO: 1. In certain embodiments, the amino acid sequence includes an Alanine (A) at the position corresponding to amino acid 173 of SEQ ID NO: 1. In some embodiments, the light activated ion channel polypeptide is comprises the amino acid sequence set forth as SEQ ID NO: 3. In some embodiments, activating the ion channel comprises contacting the ion channel polypeptide with one or more of a wavelength of a blue and a wavelength of a green light. In certain embodiments, activating the light-activated ion channel polypeptide opens the channel of the light-activated ion channel polypeptide. In some embodiments, contacting the light-activated ion channel polypeptide with a wavelength of blue or green light results in opening of the ion channel of the light-activated ion channel polypeptide, wherein the channel remains in an open state for a time period longer than an open state time period of a control light-activated ion channel polypeptide. In some embodiments the length of the time period is statistically significantly longer time period than the control open state time period. In some embodiments, the control light-activated ion channel polypeptide is a Chronos polypeptide comprising the amino acid sequence set forth as SEQ ID NO: 6. In certain embodiments, the nucleic acid sequence encoding the light-activated ion channel polypeptide comprises the nucleic acid sequence set forth as SEQ ID NO: 2. In some embodiments, the nucleic acid sequence encoding the light-activated ion channel polypeptide comprises the nucleic acid sequence set forth as SEQ ID NO: 4. In certain embodiments, the light-activated ion channel polypeptide is expressed in a membrane. In some embodiments, the membrane is a cell membrane. In some embodiments, the light-activated ion channel polypeptide is expressed in a cell. In certain embodiments, the cell is an excitable cell. In some embodiments, the cell is in a subject. In some embodiments, the membrane is a one or more of a cell membrane of: a neuronal cell, a nervous system cell, a cardiac cell, a circulatory system cell, a visual system cell, and an auditory system cell. In some embodiments, activating the light-activated ion channel polypeptide alters the ion conductivity of the membrane in which the light-activated ion channel polypeptide is expressed. In certain embodiments, activating the light-activated ion channel polypeptide depolarizes the cell in which the light-activated ion channel polypeptide is expressed.

According to an aspect of the invention, fusion proteins that include the light-activated ion channel polypeptide of any of the aforementioned embodiments or aspects of the invention are provided. In some embodiments, the fusion protein also includes one or more of a trafficking polypeptide, a signal polypeptide, an export polypeptide, and a detectable label polypeptide. In some embodiments, the light-activated ion channel polypeptide comprises the amino acid sequence set forth as SEQ ID NO: 1, SEQ ID NO: 3, or a functional variant thereof.

According to another aspect of the invention, light-activated ion channel polypeptides are provide that include an amino acid sequence set forth as SEQ ID NO: 11, SEQ ID NO: 12, SEQ ID NO: 14, SEQ ID NO: 15, SEQ ID NO: 17 or SEQ ID NO: 18, or a functional variant thereof. In certain embodiments, the light-activated ion channel polypeptide comprises the amino acid sequence set forth as SEQ ID NO: 11 with 1, 2, 3, 4, or more amino acid sequence modifications, wherein a Serine (S) is present at the amino acid position that corresponds to amino acid 170 of SEQ ID NO: 11, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth as SEQ ID NO: 11. In some embodiments, the amino acid sequence includes an alanine (A) at the amino acid position that corresponds to amino acid 198 of SEQ ID NO: 11. In some embodiments, the light-activated ion channel comprises the amino acid sequence set forth as SEQ ID NO: 14 with 1, 2, 3, 4, or more amino acid sequence modifications, wherein a Serine (S) is present at the amino acid position that corresponds to amino acid 108 of SEQ ID NO: 14, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98%, or 99% sequence identity to the sequence set forth as SEQ ID NO: 14. In some embodiments, the amino acid sequence includes an alanine (A) at the amino acid position that corresponds to amino acid 136 of SEQ ID NO: 14. In certain embodiments, the light-activated ion channel polypeptide comprises the amino acid sequence set forth as SEQ ID NO: 17 with 1, 2, 3, 4, or more amino acid sequence modifications, wherein a Serine (S) is present at the amino acid position that corresponds to amino acid 165 of SEQ ID NO: 17, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth as SEQ ID NO: 17. In some embodiments, the amino acid sequence includes an alanine (A) at the amino acid position that corresponds to amino acid 193 of SEQ ID NO: 17. In certain embodiments, activating the light-activated ion channel polypeptide opens the channel of the light-activated ion channel polypeptide. In some embodiments, activating the ion channel polypeptide with opens the ion channel of the light-activated ion channel polypeptide, and wherein the channel remains in an open state for a time period longer than an open state time period of a control light-activated ion channel polypeptide. In some embodiments the length of the time period is a statistically significant longer time period than that of the control open state time period. In some embodiments, the control light-activated ion channel polypeptide is one of a Chrimson polypeptide comprising the amino acid sequence set forth as SEQ ID NO: 10, a CoChR polypeptide comprising the amino acid sequence set forth as SEQ ID NO: 13, or a CsChR polypeptide comprising the amino acid sequence set forth as SEQ ID NO: 16. In certain embodiments, the light-activated ion channel polypeptide is expressed in a membrane. In some embodiments, the membrane is a cell membrane. In some embodiments, the light-activated ion channel polypeptide is expressed in a cell. In certain embodiments, the cell is an excitable cell. In certain embodiments, the cell is in a subject. In some embodiments, the membrane is a one or more of a cell membrane of: a neuronal cell, a nervous system cell, a cardiac cell, a circulatory system cell, a visual system cell, and an auditory system cell. In some embodiments, activating the light-activated ion channel polypeptide alters the ion conductivity of the membrane in which the light-activated ion channel polypeptide is expressed. In some embodiments, activating the light-activated ion channel polypeptide depolarizes the cell in which the light-activated ion channel polypeptide is expressed.

According to another aspect of the invention, fusion proteins that include any embodiment of an aforementioned aspect of the invention are provided. In certain embodiments, the fusion protein also includes one or more of a trafficking polypeptide, a signal polypeptide, an export polypeptide, and a detectable label polypeptide. In some embodiments, the light-activated ion channel polypeptide comprises the amino acid sequence set forth as SEQ ID NO: 11, 12, 14, 15, 17, 18, or a functional variant of thereof.

According to another aspect of the invention, polynucleotide molecules are provide that include a nucleic acid sequence encoding a light-activated ion channel polypeptide of any embodiment of any of the aforementioned light-activated ion channel polypeptides. In some embodiments, the light-activated ion channel encoded by the nucleic acid sequence is expressed in a cell.

According to another aspect of the invention, vectors that include any embodiment of any aforementioned nucleic acid sequence are provided. In certain embodiments, the nucleic acid sequence is operatively linked to a promoter sequence. In some embodiments, the vector also includes one, two, or more nucleic acid signal sequences operatively linked to the nucleic acid sequence encoding the light-activated ion channel polypeptide. In some embodiments, the vector is a plasmid vector, cosmid vector, viral vector, or an artificial chromosome. In some embodiments, the vector is in a cell. In certain embodiments, the cell is an excitable cell. In some embodiments, the cell is a vertebrate cell. In some embodiments, the cell is a mammalian cell. In certain embodiments, the cell is one or more of a neuronal cell, a nervous system cell, a cardiac cell, a circulatory system cell, a visual system cell, and an auditory system cell.

According to another aspect of the invention, methods of altering ion conductivity of a membrane are provided, the methods including: expressing in a host membrane at least one of any of embodiment of any aforementioned light-activated ion channel polypeptide and contacting the at least one of the expressed light-activated ion channel polypeptides with a light that activates at least one of the light-activated ion channels and alters the ion conductivity of the host membrane. In some embodiments, the at least one expressed light-activated ion channel polypeptides is a plurality of expressed light-activated ion channel polypeptides. In some embodiments, activating the ion channel comprises contacting the ion channel polypeptide with an activating wavelength of light. In some embodiments, the host membrane is in a cell. In certain embodiments, the cell is a neuronal cell and the method further comprises contacting the light-activated ion channel polypeptide with a light under conditions suitable to produce a spike in the neuronal cell. In some embodiments, activating the light-activated ion channel polypeptide opens the channel of the light-activated ion channel polypeptide. In some embodiments, the light-activated ion channel polypeptide includes the amino acid sequence set forth as SEQ ID NO: 1 with 1, 2, 3, 4, or more amino acid sequence modifications, wherein a Serine (S) is present at the amino acid position that corresponds to amino acid 145 of SEQ ID NO: 1, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to acids 61-295 of SEQ ID NO: 1 and at least 95%, 96%, 97%, 98%, 99% or 100% sequence identity to the remaining amino acids in the sequence set forth as SEQ ID NO: 1. In certain embodiments, the light-activated ion channel polypeptide has an Alanine (A) at the amino acid position corresponding to amino acid 173 of SEQ ID NO: 1. In some embodiments, the light activated ion channel polypeptide comprises the amino acid sequence set forth as SEQ ID NO: 11 with 1, 2, 3, 4, or more amino acid sequence modifications, wherein a Serine (S) is present at the amino acid position that corresponds to amino acid 170 of SEQ ID NO: 11, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth as SEQ ID NO: 11. In some embodiments, the amino acid sequence includes an alanine (A) at the amino acid position that corresponds to amino acid 198 of SEQ ID NO: 11. In certain embodiments, the light-activated ion channel polypeptide comprises the amino acid sequence set forth as SEQ ID NO: 14 with 1, 2, 3, 4, or more amino acid sequence modifications, wherein a Serine (S) is present at the amino acid position that corresponds to amino acid 108 of SEQ ID NO: 14, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth as SEQ ID NO: 14. In some embodiments, the amino acid sequence includes an alanine (A) at the amino acid position that corresponds to amino acid 136 of SEQ ID NO: 14. In certain embodiments, the light-activated ion channel polypeptide comprises the amino acid sequence set forth as SEQ ID NO: 17 with 1, 2, 3, 4, or more amino acid sequence modifications, wherein a Serine (S) is present at the amino acid position that corresponds to amino acid 165 of SEQ ID NO: 17, and wherein the light-activated ion-channel polypeptide has at least 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth as SEQ ID NO: 17. In some embodiments, the amino acid sequence includes an alanine (A) at the amino acid position that corresponds to amino acid 193 of SEQ ID NO: 17. In some embodiments, the host membrane is a cell membrane. In some embodiments, the cell is an excitable cell. In certain embodiments, the cell is in a subject. In some embodiments, the host membrane is a cell membrane of one or more of: a neuronal cell, a nervous system cell, a cardiac cell, a circulatory system cell, a visual system cell, and an auditory system cell. In some embodiments, activating the light-activated ion channel polypeptide alters the ion conductivity of the host membrane in which the light-activated ion channel polypeptide is expressed. In certain embodiments, activating the light-activated ion channel polypeptide depolarizes the cell in which the light-activated ion channel polypeptide is expressed. In some embodiments, the cell is a vertebrate cell. In some embodiments, the cell is a mammalian cell. In certain embodiments, the cell is a human cell. In some embodiments, the cell comprises a plurality of the light-activated ion channel polypeptides. In certain embodiments, the method also includes contacting the cell with a light that activates two or more of the plurality of the light-activated ion channel polypeptides. In some embodiments, contacting the light-activated ion channel polypeptide with an activating light results in opening of the ion channel of the light-activated ion channel polypeptide, and wherein the channel remains in an open state for a longer time period than an open state time period of a control light-activated ion channel polypeptide. In some embodiments the length of the time period is a statistically significant longer time period than that of the control open state time period. In certain embodiments, the control light-activated ion channel polypeptide is a Chronos polypeptide comprising the amino acid sequence set forth as SEQ ID NO: 6, a Chrimson polypeptide comprising the amino acid sequence set forth as SEQ ID NO: 10, a CoChR polypeptide comprising the amino acid sequence set forth as SEQ ID NO: 13, or a CsChR polypeptide comprising the amino acid sequence set forth as SEQ ID NO: 16. In some embodiments, expressing the light-activated ion channel polypeptide in the host membrane includes administering to a cell that includes the host membrane, a vector, wherein the vector includes a nucleic acid sequence encoding the light-activated ion channel and the administration of the vector results in expression of the light-activated ion channel in the host membrane. In some embodiments, the vector further comprises a signal sequence. In some embodiments, the vector also includes a cell-specific promoter. In certain embodiments, depolarizing the cell modulates a depolarization-mediated cell characteristic. In some embodiments, the depolarization-mediated cell characteristic is an action potential. In some embodiments, the depolarization-mediated cell characteristic is release of a neurotransmitter. In certain embodiments, the amino acid sequence of the light-activated ion channel is set forth as SEQ ID NO: 1, 3, 11, 12, 14, 15, 17, 18 or a functional variant thereof.

According to yet another aspect of the invention, methods of assessing the effect of a candidate compound on ion conductivity of a membrane are provided, the methods including: contacting a test membrane that includes the isolated light-activated ion channel polypeptide of any embodiment of any of the aforementioned aspects with light under conditions suitable for altering ion conductivity of the membrane; contacting the test membrane with a candidate compound; and identifying the presence or absence of a change in ion conductivity of the membrane contacted with the light and the candidate compound compared to ion conductivity in a control cell contacted with the light and not contacted with the candidate compound; wherein a change in the ion conductivity in the test membrane compared to the control indicates an effect of the candidate compound on the ion conductivity of the test membrane. In some embodiments, the membrane is in a cell. In some embodiments, altering the ion conductivity of the membrane depolarizes the cell. In some embodiments, the change is an increase in ion conductivity of the membrane. In certain embodiments, the change is a decrease in ion conductivity of the membrane. In some embodiments, the effect of the candidate compound is an effect on a depolarization-mediated cell characteristic in the test cell. In some embodiments, the method also includes characterizing the change identified in the depolarization or the depolarization-mediated cell characteristic. In certain embodiments, the depolarization-mediated cell characteristic is release of a neurotransmitter. In some embodiments, contacting the light-activated ion channel polypeptide with an activating light results in opening of the ion channel of the light-activated ion channel polypeptide, and wherein the channel remains in an open state for a statistically significant longer time period than an open state time period of a control light-activated ion channel polypeptide. In certain embodiments, the control light-activated ion channel polypeptide is a Chronos polypeptide comprising the amino acid sequence set forth as SEQ ID NO: 6, a Chrimson polypeptide comprising the amino acid sequence set forth as SEQ ID NO: 10, a CoChR polypeptide comprising the amino acid sequence set forth as SEQ ID NO: 13, or a CsChR polypeptide comprising the amino acid sequence set forth as SEQ ID NO: 16. In some embodiments, expressing the light-activated ion channel polypeptide in the test membrane comprises administering to a cell that includes the test membrane, a vector, wherein the vector comprises a nucleic acid sequence encoding the light-activated ion channel and the administration of the vector results in expression of the light-activated ion channel in the test membrane. In some embodiments, the vector also includes a signal sequence. In certain embodiments, the vector also includes a cell-specific promoter. In some embodiments, the amino acid sequence of the light-activated ion channel is set forth as SEQ ID NO: 1, 3, 11, 12, 14, 15, 17, 18, or a functional variant thereof.

According to another aspect of the invention, methods of treating a disorder in a subject are provided, the methods including administering to a subject in need of such treatment, a therapeutically effective amount of a light-activated ion channel polypeptide of any embodiment of any of the aforementioned aspects, to treat the disorder and contacting the cell with light and activating the light-activated ion channel in the cell under conditions sufficient to alter ion conductivity of a cell membrane, wherein altering the conductivity of the cell membrane treats the disorder. In some embodiments, altering the ion conductivity of the membrane depolarizes the cell. In certain embodiments, the ion conductivity comprises one or more of ion flux and proton flux across the light-activated ion channel polypeptide, or variant thereof. In some embodiments, the disease or condition is one or more of: a brain injury, a spinal cord injury, a nerve injury, epilepsy, a neurological condition, an immune system disorder, a secretory system disorder, a degenerative neurological condition, cardiac dysfunction, vision loss, blindness, deafness, and hearing loss. In some embodiments, contacting the light-activated ion channel polypeptide with an activating light results in opening of the ion channel of the light-activated ion channel polypeptide, and wherein the channel remains in an open state for a longer time period than an open state time period of a control light-activated ion channel polypeptide. In some embodiments the length of the time period is statistically significant longer time period than that of the control open state time period. In some embodiments, the control light-activated ion channel polypeptide is a Chronos polypeptide that includes the amino acid sequence set forth as SEQ ID NO: 6, a Chrimson polypeptide that includes the amino acid sequence set forth as SEQ ID NO: 10, a CoChR polypeptide that includes the amino acid sequence set forth as SEQ ID NO: 13, or a CsChR polypeptide that includes the amino acid sequence set forth as SEQ ID NO: 16. In certain embodiments, the light-activated ion channel is administered in the form of a cell, wherein the cell expresses the light-activated ion channel, or in the form of a vector, wherein the vector comprises a nucleic acid sequence encoding the light-activated ion channel and the administration of the vector results in expression of the blue-light-activated ion channel in a cell in the subject. In some embodiments, the vector also includes a signal sequence. In some embodiments, the vector also includes a cell-specific promoter. In certain embodiments, the method also includes administering an additional therapeutic composition to the subject. In some embodiments, depolarizing the cell modulates a depolarization-mediated cell characteristic. In some embodiments, the depolarization-mediated cell characteristic is an action potential. In some embodiments, the depolarization-mediated cell characteristic is release of a neurotransmitter. In certain embodiments, the amino acid sequence of the light-activated ion channel is set forth as SEQ ID NO: 1, 3, 11, 12, 14, 15, 17, 18, or a functional variant thereof.

According to another aspect of the invention, light-activated ion channel polypeptides are provided that include an amino acid sequence set forth as SEQ ID NO: 1, SEQ ID NO: 11, SEQ ID NO: 12, SEQ ID NO: 14, SEQ ID NO: 15, SEQ ID NO: 17 or SEQ ID NO: 18, or a functional variant thereof. In some embodiments, activating the light-activated ion channel polypeptide opens the channel of the light-activated ion channel polypeptide, and wherein activating the ion channel polypeptide with opens the ion channel of the light-activated ion channel polypeptide, and wherein the channel remains in an open state for a time period significantly longer than an open state time period of a control light-activated ion channel polypeptide. In certain embodiments, the control light-activated ion channel polypeptide is one of a Chronos polypeptide comprising the amino acid sequence set forth as SEQ ID NO: 6, a Chrimson polypeptide comprising the amino acid sequence set forth as SEQ ID NO: 10, a CoChR polypeptide comprising the amino acid sequence set forth as SEQ ID NO: 13, or a CsChR polypeptide comprising the amino acid sequence set forth as SEQ ID NO: 16. In some embodiments, the light-activated ion channel polypeptide is expressed in a membrane, and optionally the membrane is a cell membrane. In some embodiments, the light-activated ion channel polypeptide is expressed in a cell. In some embodiments, the cell is an excitable cell.

According to another aspect of the invention, methods of altering ion conductivity of a membrane are provided, the methods including expressing in a host membrane at least one of a light-activated ion channel polypeptide comprising an amino acid sequence set forth as SEQ ID NO: 1, SEQ ID NO: 11, SEQ ID NO: 12, SEQ ID NO: 14, SEQ ID NO: 15, SEQ ID NO: 17 and SEQ ID NO: 18, or a functional variant thereof and contacting the at least one of the expressed light-activated ion channel polypeptides with a light that activates at least one of the light-activated ion channels and alters the ion conductivity of the host membrane. In some embodiments, the host membrane is in a cell.

According to another aspect of the invention, methods of assessing the effect of a candidate compound on ion conductivity of a membrane are provided, the methods including: (a) contacting a test membrane comprising the light-activated ion channel polypeptide comprising the amino acid sequence set forth as SEQ ID NO: 1, SEQ ID NO: 11, SEQ ID NO: 12, SEQ ID NO: 14, SEQ ID NO: 15, SEQ ID NO: 17 or SEQ ID NO: 18, or a functional variant thereof with light under conditions suitable for altering ion conductivity of the membrane; (b) contacting the test membrane with a candidate compound; and (c) identifying the presence or absence of a change in ion conductivity of the membrane contacted with the light and the candidate compound compared to ion conductivity in a control cell contacted with the light and not contacted with the candidate compound; wherein a change in the ion conductivity in the test membrane compared to the control indicates an effect of the candidate compound on the ion conductivity of the test membrane. In some embodiments, the test membrane is in a test cell. In certain embodiments, altering the ion conductivity of the test membrane depolarizes the test cell.

According to another aspect of the invention, a cell is provided that comprises an embodiment of any of the aforementioned vectors. According to another aspect of the invention, a cell is provided that comprises an embodiment of any of the aforementioned aspects of light-activated ion channel polypeptides.

BRIEF DESCRIPTION OF THE DRAWINGS

FIG. 1A shows aligned amino acid sequences, set forth herein as SEQ ID NOs: 19-23. SEQ ID NO: 19 is a fragment of full-length ChR1 polypeptide, SEQ ID NO: 20 is a fragment of full-length ChR2 polypeptide; SEQ ID NO: 21 is a fragment of full-length VChR1 polypeptide; SEQ ID NO: 22 is a fragment of full-length VChR2 polypeptide; and SEQ ID NO: 23 is a fragment of full-length BR polypeptide. FIG. 1B shows schematic drawings of amino acids.

FIG. 2A shows PN3-Chronos C145S/D173A-mCherry construct. FIG. 2B shows PN3-Chronos C145S-mCherry construct. FIG. 2C shows PN3-Chronos-mCherry construct.

FIG. 3A shows normalized current traces, 20 s long. FIG. 3A shows generated photocurrent amplitudes of Chronos and two embodiments of slow kinetics mutants of the invention: a Chronos C145S single mutant polypeptide and a Chronos C145S/D173A double mutant polypeptide. Top trace (darkest) is that of the Chronos polypeptide. Of the three polypeptides, the Chronos trace shows the steepest, most rapid rise to zero after activation. The middle trace provides results of the activation of a Chronos C145S/D173A double mutant polypeptide that is followed by a slower initial rise than either of the other two traces. The trace generated using the activation conditions on an expressed Chronos C145S single mutant polypeptide showed an initial sharp upward slope followed by a less-sharp rise. An examination of photo-currents in close-up (FIG. 3B) showed that Chronos C145S/D173A double mutant had a slower photo-current activation than both Chronos and Chronos C145S single mutant. In FIGS. 3A and B show results with Chronos-mCherry (control), Chronos-C145S-mCherry (single mutant); and Chronos-C145S/D173A-mCherry (double mutant). In FIGS. 3A and B, the vertical axis is normalized photo-current; the horizontal axis is time in milliseconds; the solid box above traces indicates illumination period.

BRIEF DESCRIPTION OF THE SEQUENCES

Figure 1A:
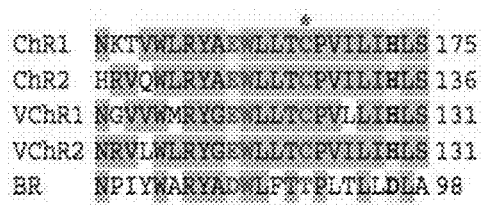
FIG. 1A-B provides sequences and a schematic diagram of amino acids.
Figure 1B:
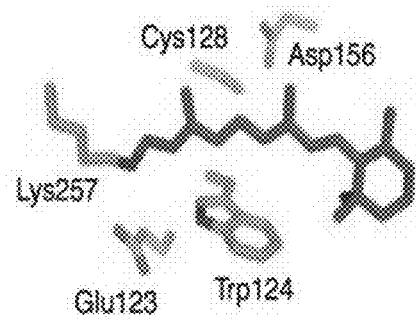

SEQ ID NO:1 is amino acid sequence of a slow Chronos mutant polypeptide (single mutant—includes C145 S).

METAATMTHAFISAVPSAEATIRGLLSAAAVVTPAADAHGETSNATTAGA

DHGCFPHINHGTELQHKIAVGLQWFTVIVAIVQLIFYGWHSFKATTGWEE

VYVCVIELVKCFIELFHEVDSPATVYQTNGGAVIWLRYSMWLLTSPVILI

HLSNLTGLHEEYSKRTMTILVTDIGNIVWGITAAFTKGPLKILFFMIGLF

YGVTCFFQIAKVYIESYHTLPKGVCRKICKIMAYVFFCSWLMFPVMFIAG

HEGLGLITPYTSGIGHLILDLISKNTWGFLGHHLRVKIHEHILIHGDIRK

TTTINVAGENMEIETFVDEEEEGGV.

SEQ ID NO: 2 is a mammalian-codon optimized DNA sequence encoding SEQ ID NO: 1, which is a slow Chronos mutant polypeptide.

atggaaacagccgccacaatgacccacgcctttatctcagccgtgcctag cgccgaagccacaattagaggcctgctgagcgccgcagcagtggtgacac cagcagcagacgctcacggagaaacctctaacgccacaacagccggagcc gatcacggttgcttccccacatcaaccacggaaccgagctgcagcacaa gatcgcagtgggactccagtggttcaccgtgatcgtggctatcgtgcagc tcatcttctacggttggcacagcttcaaggccacaaccggctgggaggag gtctacgtctgcgtgatcgagctcgtcaagtgcttcatcgagctgttcca cgaggtcgacagcccagccacagtgtaccagaccaacggaggagccgtga tttggctgcggtacagcatgtggctcctgactagccccgtgatcctgatc cacctgagcaacctgaccggactgcacgaagagtacagcaagcggaccat gaccatcctggtgaccgacatcggcaacatcgtgtggggatcacagccg cctttacaaagggccccctgaagatcctgttcttcatgatcggcctgttc tacggcgtgacttgcttcttccagatcgccaaggtgtatatcgagagcta ccacaccctgcccaaaggcgtctgccggaagatttgcaagatcatggcct acgtcttcttctgctcttggctgatgttccccgtgatgttcatcgccgga cacgagggactgggcctgatcacaccttacaccagcggaatcggccacct gatcctggatctgatcagcaagaacacttggggcttcctgggccaccacc tgagagtgaagatccacgagcacatcctgatccacggcgacatccggaag acaaccaccatcaacgtggccggcgagaacatggagatcgagaccttcgt cgacgaggaggaggagggaggagtg.

SEQ ID NO: 3 is amino acid sequence of a slow Chronos mutant polypeptide (double mutant includes C145S and D173A).

METAATMTHAFISAVPSAEATIRGLLSAAAVVTPAADAHGETSNATTAGA

DHGCFPHINHGTELQHKIAVGLQWFTVIVAIVQLIFYGWHSFKATTGWEE

VYVCVIELVKCFIELFHEVDSPATVYQTNGGAVIWLRYSMWLLTSPVILI

HLSNLTGLHEEYSKRTMTILVTAIGNIVWGITAAFTKGPLKILFFMIGLF

YGVTCFFQIAKVYIESYHTLPKGVCRKICKIMAYVFFCSWLMFPVMFIAG

HEGLGLITPYTSGIGHLILDLISKNTWGFLGHHLRVKIHEHILIHGDIRK

TTTINVAGENMEIETFVDEEEEGGV.

SEQ ID NO: 4 is a mammalian-codon optimized DNA sequence encoding SEQ ID NO: 3, which is a slow Chronos mutant polypeptide.

atggaaacagccgccacaatgacccacgcctttatctcagccgtgcctag cgccgaagccacaattagaggcctgctgagcgccgcagcagtggtgacac cagcagcagacgctcacggagaaacctctaacgccacaacagccggagcc gatcacggttgcttccccacatcaaccacggaaccgagctgcagcacaa gatcgcagtgggactccagtggttcaccgtgatcgtggctatcgtgcagc tcatcttctacggttggcacagcttcaaggccacaaccggctgggaggag gtctacgtctgcgtgatcgagctcgtcaagtgcttcatcgagctgttcca cgaggtcgacagcccagccacagtgtaccagaccaacggaggagccgtga tttggctgcggtacagcatgtggctcctgactagccccgtgatcctgatc cacctgagcaacctgaccggactgcacgaagagtacagcaagcggaccat gaccatcctggtgaccgcaatcggcaacatcgtgtggggatcacagccg cctttacaaagggccccctgaagatcctgttcttcatgatcggcctgttc tacggcgtgacttgcttcttccagatcgccaaggtgtatatcgagagcta ccacaccctgcccaaaggcgtctgccggaagatttgcaagatcatggcct acgtcttcttctgctcttggctgatgttccccgtgatgttcatcgccgga cacgagggactgggcctgatcacaccttacaccagcggaatcggccacct gatcctggatctgatcagcaagaacacttggggcttcctgggccaccacc tgagagtgaagatccacgagcacatcctgatccacggcgacatccggaag acaaccaccatcaacgtggccggcgagaacatggagatcgagaccttcgt cgacgaggaggaggagggaggagtg.

SEQ ID NO: 5 is transmembrane region of SEQ ID Nos: 1 and 3, that includes residues corresponding to amino acids 61-295 of SEQ ID NO: 1, which is a slow Chronos mutant polypeptide.

GTELQHKIAVGLQWFTVIVAIVQLIFYGWHSFKATTGWEEVYVCVIELVK

CFIELFHEVDSPATVYQTNGGAVIWLRYSMWLLTCPVILIHLSNLTGLHE

EYSKRTMTILVTDIGNIVWGITAAFTKGPLKILFFMIGLFYGVTCFFQIA

KVYIESYHTLPKGVCRKICKIMAYVFFCSWLMFPVMFIAGHEGLGLITPY

TSGIGHLILDLISKNTWGFLGHHLRVKIHEHILIH.

SEQ ID NO: 6 is amino acid sequence of Chronos (ChR90) polypeptide (See PCT Publication No. WO 2013/071231)

METAATMTHAFISAVPSAEATIRGLLSAAAVVTPAADAHGETSNATTAGA

DHGCFPHINHGTELQHKIAVGLQWFTVIVAIVQLIFYGWHSFKATTGWEE

VYVCVIELVKCFIELFHEVDSPATVYQTNGGAVIWLRYSMWLLTCPVILI

HLSNLTGLHEEYSKRTMTILVTDIGNIVWGITAAFTKGPLKILFFMIGLF

YGVTCFFQIAKVYIESYHTLPKGVCRKICKIMAYVFFCSWLMFPVMFIAG

HEGLGLITPYTSGIGHLILDLISKNTWGFLGHHLRVKIHEHILIHGDIRK

TTTINVAGENMEIETFVDEEEEGGV.

SEQ ID NO: 7 is a mammalian-codon optimized DNA sequence encoding ChR90 light-activated ion channel polypeptide (See PCT Publication No. WO 2013/071231)

atggaaacagccgccacaatgacccacgcctttatctcagccgtgcctag cgccgaagccacaattagaggcctgctgagcgccgcagcagtggtgacac cagcagcagacgctcacggagaaacctctaacgccacaacagccggagcc gatcacggttgcttccccacatcaaccacggaaccgagctgcagcacaa gatcgcagtgggactccagtggttcaccgtgatcgtggctatcgtgcagc tcatcttctacggttggcacagcttcaaggccacaaccggctgggaggag gtctacgtctgcgtgatcgagctcgtcaagtgcttcatcgagctgttcca cgaggtcgacagcccagccacagtgtaccagaccaacggaggagccgtga tttggctgcggtacagcatgtggctcctgacttgccccgtgatcctgatc cacctgagcaacctgaccggactgcacgaagagtacagcaagcggaccat gaccatcctggtgaccgacatcggcaacatcgtgtggggatcacagccg cctttacaaagggccccctgaagatcctgttcttcatgatcggcctgttc tacggcgtgacttgcttcttccagatcgccaaggtgtatatcgagagcta ccacaccctgcccaaggcgtctgccggaagatttgcaagatcatggcct acgtcttcttctgctcttggctgatgttccccgtgatgttcatcgccgga cacgagggactgggcctgatcacaccttacaccagcggaatcggccacct gatcctggatctgatcagcaagaacacttggggcttcctgggccaccacc tgagagtgaagatccacgagcacatcctgatccacggcgacatccggaag acaaccaccatcaacgtggccggcgagaacatggagatcgagaccttcgt cgacgaggaggaggagggaggagtg.

SEQ ID NO: 8 is the mammalian codon-optimized DNA sequence that encodes the wild-type Channelrhodopsin-2, (see: Boyden, E. et al., Nature Neuroscience 8, 1263-1268 (2005) and Nagel, G., et al. PNAS Nov. 25, 2003 vol. 100 no. 24 13940-13945), also referred to herein as ChR2:

atggactatggcggcgctttgtctgccgtcggacgcgaacttttgttcgt tactaatcctgtggtggtgaacgggtccgtcctggtccctgaggatcaat gttactgtgccggatggattgaatctcgcggcacgaacggcgctcagacc gcgtcaaatgtcctgcagtggcttgcagcaggattcagcattttgctgct gatgttctatgcctaccaaacctggaaatctacatgcggctgggaggaga tctatgtgtgcgccattgaaatggttaaggtgattctcgagttctttttt gagtttaagaatccctctatgctctaccttgccacaggacaccgggtgca gtggctgcgctatgcagagtggctgctcacttgtcctgtcatccttatcc acctgagcaacctcaccggcctgagcaacgactacagcaggagaaccatg ggactccttgtctcagacatcgggactatcgtgtgggggctaccagcgc catggcaaccggctatgttaaagtcatcttcttttgtcttggattgtgct atggcgcgaacacatttttttcacgccgccaaagcatatatcgagggttat catactgtgccaaagggtcggtgccgccaggtcgtgaccggcatggcatg gctgttttcgtgagctggggtatgttcccaattctcttcatttttgggc ccgaaggttttggcgtcctgagcgtctatggctccaccgtaggtcacacg attattgatctgatgagtaaaaattgttgggggttgttgggacactacct gcgcgtcctgatccacgagcacatattgattcacggagatatccgcaaaa ccaccaaactgaacatcggcggaacggagatcgaggtcgagactctcgtc gaagacgaagccgaggccggagccgtg.

SEQ ID NO: 9 is the amino acid sequence of the wild-type Channelrhodopsin-2, (see: Boyden, E. et al., Nature Neuroscience 8, 1263-1268 (2005) and Nagel, G., et al. PNAS Nov. 25, 2003 vol. 100 no. 24 13940-13945), also referred to herein as ChR2:

MDYGGALSAVGRELLFVTNPVVVNGSVLVPEDQCYCAGWIESRGTNGAQT

ASNVLQWLAAGFSILLLMFYAYQTWKSTCGWEEIYVCAIEMVKVILEFFF

EFKNPSMLYLATGHRVQWLRYAEWLLTCPVILIHLSNLTGLSNDYSRRTM

GLLVSDIGTIVWGATSAMATGYVKVIFFCLGLCYGANTFFHAAKAYIEGY

HTVPKGRCRQVVTGMAWLFFVSWGMFPILFILGPEGFGVLSVYGSTVGHT

IIDLMSKNCWGLLGHYLRVLIHEHILIHGDIRKTTKLNIGGTEIEVETLV

EDEAEAGAV.

SEQ ID NO: 10 is amino acid sequence of Chrimson polypeptide:

MAELISSATRSLFAAGGINPWPNPYHHEDMGCGGMTPTGECFSTEWWCDP

SYGLSDAGYGYCFVEATGGYLVVGVEKKQAWLHSRGTPGEKIGAQVCQWI

AFSIAIALLTFYGFSAWKATCGWEEVYVCCVEVLFVTLEIFKEFSSPATV

YLSTGNHAYCLRYFEWLLSCPVILIKLSNLSGLKNDYSKRTMGLIVSCVG

MIVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAKE

FWTFLAHHLRIKIHEHILIHGDIRKTTKMEIGGEEVEVEEFVEEEDE

DTV.

SEQ ID NO: 11 is amino acid sequence of a slow Chrimson polypeptide with C170S substitution:

MAELISSATRSLFAAGGINPWPNPYHHEDMGCGGMTPTGECFSTEWWCDP

SYGLSDAGYGYCFVEATGGYLVVGVEKKQAWLHSRGTPGEKIGAQVCQWI

AFSIAIALLTFYGFSAWKATCGWEEVYVCCVEVLFVTLEIFKEFSSPATV

YLSTGNHAYCLRYFEWLLSSPVILIKLSNLSGLKNDYSKRTMGLIVSCVG

MIVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAKE

FWTFLAHHLRIKIHEHILIHGDIRKTTKMEIGGEEVEVEEFVEEEDE

DTV.

SEQ ID NO: 12 is amino acid sequence of a slow Chrimson polypeptide with C170S and C198A substitutions:

MAELISSATRSLFAAGGINPWPNPYHHEDMGCGGMTPTGECFSTEWWCDP

SYGLSDAGYGYCFVEATGGYLVVGVEKKQAWLHSRGTPGEKIGAQVCQWI

AFSIAIALLTFYGFSAWKATCGWEEVYVCCVEVLFVTLEIFKEFSSPATV

YLSTGNHAYCLRYFEWLLSSPVILIKLSNLSGLKNDYSKRTMGLIVSAVG

MIVFGMAAGLATDWLKWLLYIVSCIYGGYMYFQAAKCYVEANHSVPKGHC

RMVVKLMAYAYFASWGSYPILWAVGPEGLLKLSPYANSIGHSICDIIAKE

FWTFLAHHLRIKIHEHILIHGDIRKTTKMEIGGEEVEVEEFVEEEDE

DTV.

SEQ ID NO: 13 is amino acid sequence of CoChR polypeptide:

MLGNGSAIVPIDQCFCLAWTDSLGSDTEQLVANILQWFAFGFSILILMFY

AYQTWRATCGWEEVYVCCVELTKVIIEFFHEFDDPSMLYLANGHRVQWLR

YAEWLLTCPVILIHLSNLTGLKDDYSKRTMRLLVSDVGTIVWGATSAMST

GYVKVIFFVLGCIYGANTFFHAAKVYIESYHVVPKGRPRTVVRIMAWLFF

LSWGMFPVLFVVGPEGFDAISVYGSTIGHTIIDLMSKNCWGLLGHYLRVL

IHQHIIIYGDIRKKTKINVAGEEMEVETMVDQEDEETV.

SEQ ID NO: 14 is amino acid sequence of a slow CoChR polypeptide with C108S substitution:

MLGNGSAIVPIDQCFCLAWTDSLGSDTEQLVANILQWFAFGFSILILMFY

AYQTWRATCGWEEVYVCCVELTKVIIEFFHEFDDPSMLYLANGHRVQWLR

YAEWLLTSPVILIHLSNLTGLKDDYSKRTMRLLVSDVGTIVWGATSAMST

GYVKVIFFVLGCIYGANTFFHAAKVYIESYHVVPKGRPRTVVRIMAWLFF

LSWGMFPVLFVVGPEGFDAISVYGSTIGHTIIDLMSKNCWGLLGHYLRVL

IHQHIIIYGDIRKKTKINVAGEEMEVETMVDQEDEETV.

SEQ ID NO: 15 is amino acid sequence of a slow CoChR polypeptide with C108S and D136A substitutions:

MLGNGSAIVPIDQCFCLAWTDSLGSDTEQLVANILQWFAFGFSILILMFY

AYQTWRATCGWEEVYVCCVELTKVIIEFFHEFDDPSMLYLANGHRVQWLR

YAEWLLTSPVILIHLSNLTGLKDDYSKRTMRLLVSAVGTIVWGATSAMST

GYVKVIFFVLGCIYGANTFFHAAKVYIESYHVVPKGRPRTVVRIMAWLFF

LSWGMFPVLFVVGPEGFDAISVYGSTIGHTIIDLMSKNCWGLLGHYLRVL

IHQHIIIYGDIRKKTKINVAGEEMEVETMVDQEDEETV.

SEQ ID NO: 16 is amino acid sequence of CsChR polypeptide:

MSRLVAASWLLALLLCGITSTTTASSAPAASSTDGTAAAAVSHYAMNGFD

ELAKGAVVPEDHFVCGPADKCYCSAWLHSHGSKEEKTAFTVMQWIVFAVC

IISLLFYAYQTWRATCGWEEVYVTIIELVHVCFGLWHEVDSPCTLYLSTG

NMVLWLRYAEWLLTCPVILIHLSNLTGMKNDYNKRTMALLVSDVGCIVWG

TTAALSTDFVKIIFFFLGLLYGFYTFYAAAKIYIEAYHTVPKGICRQLVR

LQAYDFFFTWSMFPILFMVGPEGFGKITAYSSGIAHEVCDLLSKNLWGLM

GHFIRVKIHEHILVHGNITKKTKVNVAGDMVELDTYVDQDEEHDEG.

SEQ ID NO: 17 is amino acid sequence of a slow CsChR polypeptide with C165S substitution:

MSRLVAASWLLALLLCGITSTTTASSAPAASSTDGTAAAAVSHYAMNGFD

ELAKGAVVPEDHFVCGPADKCYCSAWLHSHGSKEEKTAFTVMQWIVFAVC

IISLLFYAYQTWRATCGWEEVYVTIIELVHVCFGLWHEVDSPCTLYLSTG

NMVLWLRYAEWLLTSPVILIHLSNLTGMKNDYNKRTMALLVSDVGCIVWG

TTAALSTDFVKIIFFFLGLLYGFYTFYAAAKIYIEAYHTVPKGICRQLVR

LQAYDFFFTWSMFPILFMVGPEGFGKITAYSSGIAHEVCDLLSKNLWGLM

GHFIRVKIHEHILVHGNITKKTKVNVAGDMVELDTYVDQDEEHDEG.

SEQ ID NO: 18 is amino acid sequence of a slow CsChR polypeptide with C165S and D193A substitutions:

MSRLVAASWLLALLLCGITSTTTASSAPAASSTDGTAAAAVSHYAMNGFD

ELAKGAVVPEDHFVCGPADKCYCSAWLHSHGSKEEKTAFTVMQWIVFAVCI

ISLLFYAYQTWRATCGWEEVYVTIIELVHVCFGLWHEVDSPCTLYLSTGN

MVLWLRYAEWLLTSPVILIHLSNLTGMKNDYNKRTMALLVSAVGCIVWGT

TAALSTDFVKIIFFFLGLLYGFYTFYAAAKIYIEAYHTVPKGICRQLVRL

QAYDFFFTWSMEPILFMVGPEGFGKITAYSSGIAHEVCDLLSKNLWGLMG

HFIRVKIHEHILVHGNITKKTKVNVAGDMVELDTYVDQDEEHDEG.

SEQ ID NO: 19 is amino acid sequence of a fragment of a full-length ChR1 polypeptide:

NKTVWLRYAEWLLTCPVILIHLS.

SEQ ID NO: 20 is amino acid sequence of a fragment of a full-length ChR2 polypeptide:

HRVQWLRYAEWLLTCPVILIHLS.

SEQ ID NO: 21 is amino acid sequence of a fragment of a full-length VChR1 polypeptide:

NGVVWMRYGEWLLTCPVLLIHLS.

SEQ ID NO: 22 is amino acid sequence of a fragment of a full-length VChR2 polypeptide:

NRVLWLRYGEWLLTCPVILIHLS.

SEQ ID NO: 23 is amino acid sequence of a fragment of a full-length BR polypeptide:

NPIYWARYADWLFTTPLTLLDLA.

SEQ ID NO: 24 is the DNA sequence of the ER export sequence (also referred to herein as "ER2"):

ttctgctacgagaatgaagtg.

SEQ ID NO: 25 is the amino acid sequence of the ER export sequence encoded by SEQ ID NO: 24 and also referred to herein as "ER2":

FCYENEV.

SEQ ID NO: 26 is the DNA sequence of KGC, which is a C terminal export sequence from the potassium channel Kir2.1:

aaatccagaattacttctgaagggagtatatccctctggatcaaataga catcaatgtt.

SEQ ID NO: 27 is the amino acid sequence of KGC encoded by SEQ ID NO: 26, which is a C terminal export sequence from the potassium channel Kir2.1:

KSRITSEGEYIPLDQIDINV.

SEQ ID NO: 28 is the DNA sequence of SS, which is a signal peptide that is destined towards the secretory pathway:

atggtcccgtgcacgctgctcctgctgttggcagccgccctggctccgac tcagacgcgggcc.

SEQ ID NO: 29 is the amino acid sequence of SS encoded by SEQ ID NO: 28:

MVPCTLLLLLAAALAPTQTRA.

SEQ ID NO: 30 is nucleic acid sequence of synapsin promoter, also referred to herein as "syn":

ctagactgcagagggccctgcgtatgagtgcaagtgggttttaggaccag
gatgaggcggggtgggggtgcctacctgacgaccgaccccgacccactgg
acaagcacccaaccccattccccaaattgcgcatccctatcagagagg
gggaggggaaacaggatgcggcgaggcgcgtgcgcactgccagcttcagc
accgcggacagtgccttcgccccgcctggcggcgcgcgccaccgccgcc
tcagcactgaaggcgcgctgacgtcactcgccggtcccccgcaaactccc
cttcccggccaccttggtcgcgtccgcgccgccgccggcccagccggacc
gcaccacgcgaggcgcgagataggggggcacgggcgcgaccatctgcgct
gcggcgccggcgactcagcgctgcctcagtctgcggtgggcagcggagga
gtcgtgtcgtgcctgagagcgcagtcgaga.

SEQ ID NO: 31 is nucleic acid sequence of a hemagglutinin:

tacccatacgatgttccagattacgct.

SEQ ID NO: 32 is amino acid sequence of the hemagglutinin polypeptide encoded by SEQ ID NO:

YPYDVPDYA.

DETAILED DESCRIPTION

The invention in some aspects relates to the expression in cells of stimulus-driven ion channel polypeptides that can be activated by contact with one or more pulses of light, which results in strong depolarization of the cell. Embodiments of the invention include opsin polypeptides comprising sequences that have been identified and determined to result in altered channel kinetics of the opsin molecules. Light-activated ion channel polypeptides of the invention, also referred to herein as "slow mutant" polypeptides and "slow mutant light activated ion channel" polypeptides can be expressed in specific cells, tissues, and/or organisms and used to control cells in vivo, ex vivo, and in vitro in response to pulses of light of a suitable wavelength. Specific amino acid substitutions and combinations of substitutions have now been identified that when present in a sequence of a light-activated ion channel polypeptide expressed in a membrane and contacted with an "activating" light, alter the response time and/or length of "open-state" time of the substituted light-activated ion channel polypeptide compared to the same light-activated ion channel polypeptide without the one or substitutions.

Slow mutant polypeptide sequences have now been identified that are derived from parent light-activated ion channel amino acid sequences, which are also referred to herein as "non-slow mutant" parent polypeptides or "non-slow mutant ion channel" parent polypeptides. Non-limiting examples of non-slow mutant parent polypeptides are: Chronos, Chrimson, CsChR, CoChR polypeptides. When a slow mutant polypeptide of the invention is activated with light, its ion channel remains open for a longer period of time than does the ion channel of the slow mutant's light-activated parent polypeptide under similar activation conditions. In some embodiments, the length of time the slow mutant polypeptide of the invention remains open is statistically significant compared to the shorter open time of a control light-activated ion channel polypeptide. In a non-limiting example, the ion channel of a slow mutant light-activated polypeptide that has a Chronos polypeptide parent, maintains an open time that is longer than the period of ion channel open time of its parent, when each is activated under similar conditions. Although slow mutant polypeptides of the invention have been determined to maintain a longer open time than their parents when activated, slow mutant polypeptides share certain characteristics with their respective parents. For example, though not intended to be limiting, slow mutants and their parent molecules are strongly activated by sufficient contact with a suitable wavelength light, can be delivered to cells and subjects and expressed in cell membranes using similar delivery and administration means, and activation opens the ion channel of the polypeptide. In some aspects of the invention, the parent molecule is a Chronos, Chrimson, CsChR, CoChR polypeptide or functional variant thereof, or its encoding nucleic acid. Methods to activate light-activated ion channel polypeptides such as Chronos, Chrimson, CsChR, CoChR, and variants thereof, are known in the art and include knowledge and use of variables such as, but not limited to: wavelength of contacting light, pulse length of contacting light, light pulse frequency, pattern of contact with the light, etc. In some embodiments of the invention, these and other art-known methods can be used to activate a corresponding slow mutant polypeptide of the invention and to open the channel of the slow mutant polypeptide.

Optogenetic tools such as light-activated ion channel polypeptides are used in many fields, including but not limited to, in research and in therapeutic preclinical and clinical applications. However, due to the level of expression of light-activated polypeptides that may be achieved in neurons, contact with sufficient light is necessary to activate the expressed polypeptides. Light levels needed to activate previously known light-activated ion channel polypeptides may be greater than 1 mW mm$^{-2}$ intensity and must be applied to tissue in which light-activated polypeptides are expressed over the time period in which depolarization is required, which has been difficult in long time-scale experiments. The slow mutant light-activated channel polypeptides of the invention differ from prior light-activated ion channel polypeptides in that when a slow mutant polypeptide of the invention is contacted with light and its channel opens, the channel remains open for a period of time that permits less light to be used to maintain sufficient activation as compared to the light required for use of non-slow mutant ion channel polypeptides. Thus, slow mutant polypeptides of the invention can be used in experiments, treatments, and other methods for which previously known non-slow mutant light activated ion channel polypeptides have been used, but the use of slow mutant polypeptides permit activation and open times to be maintained with less light exposure and contact, thereby reducing negative effects associated with longer light exposure.

Embodiments of light-activated ion channel polypeptides of the invention, as compared to prior light-activated polypeptides have an increased responsiveness to lower levels of activating light. Because photocurrent amplitudes at a given light intensity are set, at least in part, by a balance between recruitment of new open states and transition to the closed state, the extended length "open time" of slow mutant polypeptide ion channels of the invention may result in increased photocurrent, under lower light exposure conditions. For example, contact of a plurality of slow mutant light-activated ion channel polypeptides of the invention expressed in cells with a suitable activating light can result in increased accumulations of the channels in the plurality of polypeptides that are in the open state, which results in effectively increased responsiveness at lower light levels compared to previously known light-activated ion channel polypeptides.

The invention, in part, includes slow mutant light-activated ion channel polypeptides in which amino acid substitutions have been made in the amino acid sequence of a parent light activated ion channel polypeptide that includes in the structural helix known as helix 3 of the seven transmembrane helices in the polypeptide. Amino acid substitutions in slow mutants of the invention result in reduced interactions between the altered polypeptide region and the all-trans retinal Schiff base (RSB) chromophore. Slow mutants of the invention include changes in the amino acid sequence that interfere with the RSB and can be used in methods such as, but not limited to: color tuning; accumulating conducting states of the channels in a cell, membrane, and/or organism; and altering ion channel kinetics—for example, determining the duration of the open state of the ion channel following its activation. This characteristic of embodiments of light-activated ion channels of the invention is also referred to herein as: "increasing accumulations of the open state", maintaining "open-state", longer "open time", and increased "open-time" of the ion channel.

Slow mutant ion channel polypeptides, like their parent light-activated ion channel polypeptides, can be expressed in specific cells, tissues, and/or organisms and used to control cells in vivo, ex vivo, and in vitro in response to pulses of light of a suitable activating wavelength. Slow mutant polypeptides have now been identified that comprise a single amino acid substitution or a double amino acid substitution in a parent light-activated ion channel polypeptide sequence. Certain slow mutant polypeptides of the invention are derived from parent polypeptides such as Chronos, Chrimson, CsChR, CoChR, and functional variants of each of each thereof and include one or two specific amino acid substitutions to the parent sequences that have now been identified as resulting in an extended channel open time after activation, as compared to the open time of the channel of the parent polypeptide under similar conditions.

Certain embodiments of slow mutant polypeptides of the invention differ from their parent polypeptides in that following light activation a slow mutant maintains the open state for a statistically significant longer period of time than the time period of the open state of its parent polypeptide under the same activation conditions. In some aspects of the invention, the parent is a Chronos, Chrimson, CsChR, or CoChR polypeptide, polynucleotide, or a functional variant of a Chronos, Chrimson, CsChR, or CoChR polypeptide or its encoding polynucleotide.

A non-limiting example of a slow mutant molecule of the invention is a slow mutant Chronos polypeptide or polynucleotide, for example a slow mutant polypeptide comprising the amino acid sequence of the Chronos polypeptide sequence set forth herein as SEQ ID NO: 6, that includes one or more amino acid substitutions that result in characteristics of a slow mutant light-activated ion channel polypeptide. The slow mutant of a Chronos polypeptide or its encoding nucleic acid sequence is described herein as having the Chronos polypeptide or encoding polynucleotide, respectively as its "parent" molecule. A slow mutant polypeptide of the invention may comprise the amino acid of its parent polypeptide that includes one or more amino acid substitutions. In some embodiments the slow mutant of the invention comprises its parent Chronos amino acid sequence with the single amino acid substitution or double amino acid substitution, as set forth as SEQ ID NO: 1 and SEQ ID NO: 3, respectively. It will be understood that a functional variant of SEQ ID NO: 6 may also be a parent molecule for a slow mutant of the invention and that a slow mutant polypeptide of the invention for which a functional variant of a light-activated ion channel polypeptide such as Chronos, Chrimson, ScChR, or CoChR is the parent polypeptide may comprise the amino acid sequence of the functional variant with the single amino acid substitution or double amino acid substitutions that correspond to the substitutions shown in Table 1.

TABLE 1

Identification of substituted residues in positions corresponding to parent amino acid sequence

| Parent Name and SEQ ID NO | Single Substitution in Slow Mutant | Double Substitutions in Slow Mutant |
|---|---|---|
| Chronos (SEQ ID NO: 6) | C145S | C145S and D173A |
| Chrimson (SEQ ID NO: 10) | C170S | C170S and C198A |
| CoChR (SEQ ID NO: 13) | C108S | C108S and D136A |
| CsChR (SEQ ID NO: 16) | C165S | C165S and D193A |

Illumination and Activation

Slow mutant molecules of the invention, include, but are not limited to slow mutant Chronos, slow mutant Chrimson, slow mutant CoChR, slow mutant CsChR, and functional variants thereof [see Klapoetke et al. (2014) Nature Methods 11(3), 338-346; and Yizhar, O. et al. (2011) Neuron Vol. 71:9-34; the content of each of which is incorporated by reference herein in its entirety.] Methods to prepare and express previously known light-activated ion channel molecules can be used in conjunction with the slow mutant molecules described herein. Slow mutant polypeptides of the invention can be used in art-known methods such as, but not limited to: compound screening, altering cell voltage and/or electrical activity in cells, and therapeutic methods, which have been described in conjunction with previously known light-activated ion channel molecules.

Slow mutant polypeptides of the invention can be expressed in fusion proteins and used in optogenetic methods and compositions. Embodiments of methods of the invention include expressing a slow mutant polypeptide of the invention in a cell and contacting the polypeptide with light suitable to activate the polypeptide and open the slow mutant polypeptide channel. Methods to prepare and express a light-activated ion channel polypeptide in a cell and/or in a subject are well known in the art, as are methods to select and apply a suitable wavelength of light to the cell in which the light-activated ion channel is expressed under suitable conditions to activate the expressed ion channel polypeptide in the cell.

Specific ranges of wavelengths of light that in some embodiments of the invention are useful to activate ion channels of the invention are provided and described herein. It will be understood that a light of appropriate wavelength for activation and will have a power and intensity appropriate for activation. It is well known in the art that light pulse duration, intensity, and power are parameters that can be altered when activating a channel with light. Thus, one skilled in the art will be able to adjust power, intensity appropriately when using a wavelength taught herein or known in the art to activate a light-activated ion channel of the invention. A dose light that contacts a light-activated ion channel of the invention may be determined based on the wavelength, pulse length, and power of the light that contacts the light-activated ion channel. Thus, as a non-limiting example, a dose may have a wavelength of 550 nm, a 4 ms pulse length, and a 0.5 mW/mm$^2$ power and another light dose may have a wavelength of 550 nm, a 3 ms pulse length and a 0.5 mW/mm$^2$ power. Those skilled in the art will understand methods to select a dose of light by independently selecting a wavelength, a pulse length, and a power for the light with which a light-activated ion channel of the invention is contacted.

In some embodiments of the invention, wavelength and pulse length may be held steady, and power incrementally increased to examine activation parameters of a light-activated ion channel of the invention. Similarly, in certain embodiments of the invention may include incremental wavelength increases while pulse length and power are held steady; or incremental pulse length increases while wavelength and power are held steady. In some embodiments of the invention two or more of wavelength, pulse length, and power of a light may be incrementally altered to examine the effect on activation of a light-activating ion channel of the invention. It will be understood that illumination parameters for activating a parent Chronos, Chrimson, CoChR, or CsChR light-activated ion channel polypeptide that open the polypeptide channel can be used in some embodiments of the invention to activate a slow mutant polypeptide of the invention that is a child of the Chronos, Chrimson, ChChR, or CsChR parent polypeptide, respectively.

Methods of adjusting illumination variables for activating light-activated ion channel polypeptides are well-known in the art and may be applied to activate slow mutant polypeptides of the invention. One example of a benefit of using a slow mutant polypeptide of the invention is the ability to "tune" the polypeptide's response (for example, opening, rate of opening, open-time, etc.) using appropriate illumination variables (e.g., wavelength, intensity, duration, etc.), which also referred to herein as dose, to activate the channel. Methods of adjusting illumination variables are well known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19):8143-8. Epub 2007 May 1, each of which is incorporated herein by reference in its entirety. It is possible to utilize a narrow range of one or more illumination variables to activate a slow mutant polypeptide of the invention.

Light-Activated Ion Channel Molecules

A slow mutant polypeptide of the invention can be expressed in a cell membrane and comprises an ion channel that opens upon activation of the slow mutant polypeptide by contact with light under suitable conditions. An ion channel is an integral membrane protein that forms a pore through a membrane and assist in establishing and modulating the small voltage gradient that exists across the plasma membrane of all cells and are also found in subcellular membranes of organelles such as the endoplasmic reticulum (ER), mitochondria, etc. When a light-activated ion channel of the invention is activated by contacting the cell with appropriate light, the pore opens and permits conductance of ions such as sodium, potassium, calcium, etc. through the pore.

Slow mutant polypeptides of the invention permit ion conductance and depolarization when contacted under suitable conditions with an appropriate wavelength of light. As will be understood by those in the art, the term "depolarized" used in the context of cells means an upward change in the cell voltage. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold an action potential (e.g. a spike) results. In some embodiments of the invention, activation of the slow mutant polypeptides expressed in a cell membrane results in the voltage of the cell becoming less negative and rising by at least about 20, 30, 40, 50, 60, 70, 80, 90, 100 mV (depending on the cell type) thus, depolarizing the cell. As used herein, the term "activate" when used in reference to a slow mutant polypeptide of the invention, means to open the channel making it permissive to ion conduction and passage through the channel.

It has been identified that activating a plurality of at least one slow mutant polypeptide of the invention expressed in a cell or plurality of cells, results in a channel open-time that permits less illumination to be used to activate the channels, as compared to non-slow mutant polypeptides under similar conditions. The channels of activated slow mutant polypeptides remain open for a longer period of time than channels of the slow mutants' parent polypeptides when they are activated under similar conditions.

In some embodiments of the invention, light-activated channels may be used to modify the transmembrane potential (and/or ionic composition) of cells (and/or their subcellular regions, and their local environment). For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of light-activated ion channels in one, two, three, or more (e.g. a plurality) of cells in a tissue or organism, can result in depolarization of the single cell or the plurality of cells by contacting the light-activated ion channels with light of suitable wavelength.

The invention, in part, also includes polynucleotides comprising nucleic acid sequences that encode slow mutant polypeptides and functional variants thereof of the invention as well as vectors and constructs that comprise such nucleic acid sequences. In some embodiments the invention includes expression in cells, tissues, and subjects of slow mutant polypeptides encoded by the nucleic acid sequences. In certain embodiments, the invention comprises methods for preparing and included in vectors genes that encode slow mutant polypeptides of the invention. The vectors may be delivered into, also referred to herein as: "administered to" a cell and/or subject and the encoded slow mutant polypeptide expressed in the cell and/or subject.

The invention, in part, includes isolated nucleic acids comprising sequences that encode light-activated ion channels of the invention as well as vectors and constructs that comprise such nucleic acid sequences. Light-activated ion channel polypeptides of the invention may be part of fusion proteins. Thus, a fusion protein may comprise a light-activated ion channel of the invention and may be used in methods of the invention. Also encompassed by embodiments of the invention are methods for preparing and using genes that encode slow mutant light-activated ion polypeptides, including, but not limited to, expressing in cells, tissues, and organisms, one or more slow mutant polypeptides encoded by the nucleic acid sequences. The terms, "protein," "polypeptides," and "peptides" are used interchangeably herein.

Sequences

The present invention, in part, includes novel light-activated ion channels polypeptides and methods of their use in cells and subjects. Non-limiting examples of sequences of slow mutant polypeptides of the invention are set forth herein as SEQ ID NO: 1, 3, 11, 12, 14, 15, 17, and 18. The slow mutant polypeptides of the invention also include functional variants of polypeptides set forth as SEQ ID NOs: 1, 3, 11, 12, 14, 15, 17, and 18.

A functional variant or modified slow mutant polypeptide of the invention versus its parent slow mutant polypeptide may comprise (1) substitutions of at least 1, 2, 3, 4, 5, 6, 7, 8, 9, 10, or more amino acids, (2) insertions and/or deletions of at least 1, 2, 3, 4, 5, 6, 7, 8, 9, 10, or more amino acids at one or several positions. It will be understood that modification or change in a parent slow mutant polypeptide amino acid sequence will not include a change in the single or double substitutions identified in Table 1. Thus, for example, a functional variant of SEQ ID NO: 1 may include one or more substitutions, deletions, and/or insertions to the sequence of SEQ ID NO: 1, but will include a serine in the position that corresponds to amino acid 145 of SEQ ID NO: 1. Similarly, a functional variant of SEQ ID NO: 12 may include one or more substitutions, deletions, and/or insertions to the sequence of SEQ ID NO: 12, but will include a serine in the position that corresponds to amino acid 170 and an alanine in the position that corresponds to amino acid 198 of SEQ ID NO: 12. Selection and preparation of sequence modifications in slow light-activated ion channel polypeptides of the invention for preparation and use of functional variants can be carried out using routine methods. Extensive information on modifications that can be include that will not eliminate function of a slow light-activated ion channel polypeptide is available in the art. [See for example, see: Klapoetke et al, (2014) *Nature Methods*, March; 11(3):338-346 including supplement, the entire content of which is incorporated herein by reference.]

A functional variant of a slow mutant polypeptide of the invention may have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, amino acid sequence identity with its parent slow mutant polypeptide. Thus, a functional variant of SEQ ID NO: 1, 3, 11, 12, 14, 15, 17, or 18 has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, amino acid sequence identity with its parent slow mutant polypeptide: SEQ ID NO: 1, 3, 11, 12, 14, 15, 17, or 18, respectively. As used herein, the term "identity" refers to the degree of relatedness between two or more polypeptide sequences, which may be determined by the match between the sequences. The percentage is obtained as the percentage of identical amino acids in two or more sequences taking account of gaps and other sequence features. The identity between polypeptide sequences can be determined by means of known procedures. Algorithms and programs are available and routinely used by those in the art to determine identity between polypeptide sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

A non-limiting example of a functional variant of SEQ ID NO: 1 has the amino acid sequence set forth as SEQ ID NO: 1 including serine at the position corresponding to residue 145 of SEQ ID NO: 1, but includes modifications comprising one or more of substitutions: A18G, A36G, D51E, I68V, A94G, I113L, I113V, R165K, A210G, and I257V. A non-limiting example of a functional variant of SEQ ID NO: 3 has the amino acid sequence set forth as SEQ ID NO: 3 including the serine and alanine at positions corresponding to residues 145 and 173, respectively of SEQ ID NO: 3, but includes modifications comprising one or more of substitutions: A18G, A36G, D51E, I68V, A94G, I113L, I113V, R165K, A210G, and I257V. A non-limiting example of a functional variant of SEQ ID NO: 11 has the amino acid sequence set forth as SEQ ID NO: 11 including the serine at the position corresponding to residue 170 of SEQ ID NO: 11, but includes modifications comprising one or more of substitutions: A8G, D29E, D56E, R85K, A101G, A119G, I221L, and I221V. A non-limiting example of a functional variant of SEQ ID NO: 12 has the amino acid sequence set forth as SEQ ID NO: 12 including the serine and alanine at positions corresponding to residues 170 and 198, respectively of SEQ ID NO: 12, but includes modifications comprising one or more of substitutions: A8G, D29E, D56E, R85K, A101G, A119G, I221L, and I221V. A non-limiting example of a functional variant of SEQ ID NO: 14 comprises the amino acid sequence set forth as SEQ ID NO: 14 including the serine at the position corresponding to residue 108 of SEQ ID NO: 14, but includes modifications comprising one or more of substitutions: D21E, I44L, I44V, R56K, I75L, I75V, I156L, I156V, and D223E. A non-limiting example of a functional variant of SEQ ID NO: 15 comprises the amino acid sequence set forth as SEQ ID NO: 15 including serine and alanine at positions corresponding to residues 108 and 136, respectively of SEQ ID NO: 15, but includes modifications comprising one or more of substitutions: D21E, I44L, I44V, R56K, I75L, I75V, I156L, I156V, and D223E. A non-limiting example of a functional variant of SEQ ID NO: 17 comprises the amino acid sequence set forth as SEQ ID NO: 17 including the serine at the position corresponding to residue 165 of SEQ ID NO: 17, but includes modifications comprising one or more of substitutions: A12G, D50E, A88G, A108G, I126L, I126V, R157K, R246K, and A279G. A non-limiting example of a functional variant of SEQ ID NO: 18 comprises the amino acid sequence set forth as SEQ ID NO: 18 including the serine and alanine at positions corresponding to residues 165 and 193, respectively of SEQ ID NO: 18, but includes sequence modifications comprising one or more of substitutions: A12G, D50E, A88G, A108G, I126L, I126V, R157K, R246K, and A279G.

TABLE 2

Non-limiting examples of substituted slow light-activated ion channel polypeptides of the invention, each also referred to herein a variant of its parent sequence. Each of the below examples shows from 1 to 5 amino acid substitutions to a parent sequence.

| Parent SEQ ID | Additional Modification | Additional Modification | Additional Modification | Additional Modification | Additional Modification |
|---|---|---|---|---|---|
| SEQ ID NO: 1 | A18G | | | | |
| SEQ ID NO: 1 | A18G | D51E | | | |
| SEQ ID NO: 1 | A18G | D51E | I113L | | |
| SEQ ID NO: 1 | I113L | A210G | | | |
| SEQ ID NO: 1 | A36G | I113V | A210G | I257V | |
| SEQ ID NO: 3 | A18G | | | | |
| SEQ ID NO: 3 | I113L | | | | |
| SEQ ID NO: 3 | D51E | A94G | A210G | | |
| SEQ ID NO: 3 | A36G | A94G | I113V | A210G | I257V |
| SEQ ID NO: 11 | A8G | D56E | | | |
| SEQ ID NO: 11 | D29E | R85K | A119G | I221V | |
| SEQ ID NO: 11 | A8G | D56E | R85K | A119G | I221L |
| SEQ ID NO: 11 | D56E | A119G | | | |
| SEQ ID NO: 12 | A8G | | | | |
| SEQ ID NO: 12 | A101G | | | | |
| SEQ ID NO: 12 | D29E | R85K | I221V | | |
| SEQ ID NO: 12 | A8G | D56E | A101G | A119G | I221L |
| SEQ ID NO: 14 | D21E | | | | |
| SEQ ID NO: 14 | I75L | I156V | | | |
| SEQ ID NO: 14 | I44L | R56K | I156L | D223E | |
| SEQ ID NO: 14 | D21E | I44V | R56K | I75L | I156V |
| SEQ ID NO: 15 | D21E | | | | |
| SEQ ID NO: 15 | I44V | I75L | I157L | D223E | |
| SEQ ID NO: 15 | D21E | I44L | I75V | I156V | D223E |
| SEQ ID NO: 15 | I75V | D223E | | | |
| SEQ ID NO: 17 | A12G | A88G | | | |
| SEQ ID NO: 17 | D50E | | | | |
| SEQ ID NO: 17 | A12G | A108G | R157K | R246K | A279G |
| SEQ ID NO: 17 | I126V | R157K | | | |
| SEQ ID NO: 18 | A12G | | | | |
| SEQ ID NO: 18 | A88G | I126L | | | |
| SEQ ID NO: 18 | D50E | A88G | I126V | R157K | A279G |
| SEQ ID NO: 18 | I126V | R246K | | | |

One skilled in the art will understand that slow mutant light-activated ion channels of the invention can be identified based on sequence similarity to a slow mutant polypeptide disclosed and described herein. It will be understood that additional slow mutant polypeptides may be identified using sequence alignment with one of the slow mutant polypeptides sequences or functional variants thereof described herein. Sequence identity can be determined using standard techniques known in the art.

For slow mutant polypeptides and variants thereof of the invention, the presence of functionality, e.g., activation of a channel by contact with suitable light, length of open-time of a channel, brightness of illumination required for activation, etc. can be determined using methods described herein, and functional variants of slow mutant polypeptides of the invention can be used in methods described herein. It is understood that the level of sequence identity with a slow mutant polypeptide of the invention plus functionality with respect to activation by suitable light, open-time, and other illumination variables can be characteristics used to identify additional slow mutant polypeptides using standard procedures for sequence alignment, comparisons, assays for channel polypeptide activation, and assays for ion channel activity.

Slow mutant light-activated ion channels of the invention are transmembrane channel polypeptides that use light energy to open, permitting ion conductance through their pore, thus altering the potential of the membrane in which they are expressed. A non-limiting example of an ion that can be moved through a pore of the invention includes a sodium ion, a potassium ion, a calcium ion, a proton, etc. Routine methods may be used to measure different ion currents for light-activated ion channels of the invention. Slow mutant polypeptides of the invention can be activated by sustained light and/or by light pulses and the ion conductance resulting from activation of a slow mutant polypeptides of the invention can depolarize cells and alter the voltage in cells and organelles in which they are expressed.

In non-limiting examples of implementations, the invention comprises methods for preparing and using genes encoding light-activated ion channels of the invention that have now been identified. The invention, in part, also includes isolated nucleic acids comprising sequences that encode light activated ion channels of the invention as well as vectors and constructs that comprise such nucleic acid sequences. In some embodiments the invention includes expression of polypeptides encoded by the nucleic acid sequences, in cells, tissues, and organisms.

The slow mutant polypeptides and their encoding nucleic acid sequences used in aspects and methods of the invention may be "isolated" sequences. As used herein, the term "isolated" used in reference to a polynucleotide, nucleic acid, amino acid sequence, or polypeptide of the invention, means a polynucleotide sequence, nucleic acid, amino acid sequence or polypeptide that is present in sufficient quantity to permit its identification or use. An isolated nucleic acid or polypeptide of the invention is a nucleic acid or polypeptide that is not part of or included in a wild-type cell or organism that is a native organism/cell for its parent molecule. For example, a parent nucleic acid or polypeptide may be naturally present in a cell or organism of a Chloromonas, Chlamydomonas, Stigeoclonium, or other bacterial family, and an isolated slow mutant polypeptide or encoding nucleic acid is a slow mutant molecule that is not located in a cell or organism of a bacterial family.

A polypeptide or encoding nucleic acid of a slow mutant of the invention that is present in a cell, tissue, and/or organism, etc., is considered to be in a 'host' cell, tissue, and/or organism, respectively. Non-limiting examples of a host membrane, cell, or tissue include: mammalian, non-human primate, vertebrate, invertebrate, fish, reptile, crustaceans, insect, and avian membranes, cells, and tissues. Non-limiting examples of a host organism or subject include: humans, non-human primates, vertebrates, invertebrates, mammals, insects, fish, crustaceans, reptiles, and birds.

Slow Mutant Sequences Including Modified Sequences

A slow mutant molecule of the invention may comprise an amino acid sequence that is modified from its "parent" sequence and the invention, in part, includes functional variants of slow mutant molecules set forth herein. As used herein, a functional variant is a molecule that retains some or all of one or more functions of its parent sequence, but has been modified from the parent sequence. As used herein the term "modified" or "modification" in reference to a nucleic acid or polypeptide sequence refers to a change of one, two, three, four, five, six, or more residues in the modified sequence as compared to its parent sequence, which is also referred to herein as the sequence from which it was derived. For example, a modified polypeptide sequence may be identical to its parent polypeptide sequence except that it has one, two, three, four, five, or more amino acid substitutions, deletions, insertions, or combinations thereof. In some embodiments of the invention a modified sequence may include one, two, three, four, or more amino acid substitutions in a parent polypeptide sequence. In aspects of an invention, a functional variant of a slow mutant polypeptide or its encoding polynucleotide has the sequence of its parent slow mutant polypeptide or its encoding polynucleotide, respectively, but with one, two, three, four, five, or more sequence modifications and still retaining at some or all of one or more functions of the parent molecule.

Sequences of slow mutant polypeptides provided herein can be modified with one or more substitutions, deletions, insertions, or other modifications and such modified light-activated ion channels can be tested using methods described herein for characteristics including, but not limited to: expression, cell localization, activation, open-time, recover, and depolarization in response to contact with light using methods disclosed herein. In some embodiments, the invention includes the use of targeted site-directed mutagenesis at specific amino acid residues of a slow mutant polypeptide of the invention including but not limited to residues of one or more of SEQ ID Nos: 1, 3, 11, 12, 14, 15, 17, and 18. Specific locations for single mutations can be identified and alone, or in combination with two or more additional mutations can be placed into a slow mutant sequence and tested with respect to characteristics such as, but not limited to: their activation, open-time, and photo-current amplitude. Thus, sequences of slow mutant polypeptides of the invention can be modified and the resulting polypeptides tested for various characteristics, and used in methods disclosed herein.

Non-limiting examples of modifications that can be included in slow mutant polypeptides of the invention are conservative amino acid substitutions, which may produce molecules having functional characteristics similar to those of the molecule from which such modifications are made. Conservative amino acid substitutions are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution because both are similarly sized negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) [see, e.g., Creighton, Proteins, W.H. Freeman, New York (1984)]. Slow mutant polypeptides that include modifications, including but not limited to one, two, three, four, or more conservative amino acid substitutions can be identified and tested for characteristics including, but not limited to: expression, cell localization, activation, open-time, and depolarization and depolarization-effects in response to contact with light using methods disclosed herein.

Slow mutant polypeptides of the invention may be shorter or longer than their parent light-activated ion channel polypeptide sequences. Thus, a slow mutant polypeptide may be a full-length polypeptide or functional fragment thereof. In addition, polynucleotides of the invention may be used to obtain additional coding regions, and thus additional slow mutant polypeptide sequences, using techniques known in the art.

In some aspects of the invention, functional variants of a slow mutant polypeptide sequence may have at least 80%, 81%, 82%, 83%, 84%, 85%, 86%, 87%, 88%, 89%, 90%, 91%, 92%, 93%, 94%, 95%, 96%, 97%, 98%, or 99% or 100% identity to a parent slow mutant or to another light-activated ion channel polypeptide sequence disclosed herein, non-limiting examples of which include CoChR, CsChR, Chrimson, Chronos, etc. Art-known alignment methods and tools can be used to align substantially similar sequences permitting positional identification of amino acids that may be modified as described herein to prepare a slow mutant polypeptide of the invention or its encoding polynucleotide. Standard sequence analysis tools and computer programs, such as those used for alignment, etc. can be used to identify slow mutant molecules of the invention that share one or more functional properties with a slow mutant light-activated ion channel described herein.

Sequence modifications can be in one or more of three classes: substitutions, insertions, or deletions. These modified sequences, (which may also be referred to as variants, or derivatives) may be prepared by site-specific mutagenesis of nucleic acids in the DNA encoding a light-activated ion channel polypeptide, using cassette or PCR mutagenesis or other techniques known in the art, to produce DNA encoding the modified light-activated ion channel polypeptide, and thereafter expressing the DNA in recombinant cell culture, cells, and/or subjects. Amino acid sequence variants are characterized by the predetermined nature of the variation, a feature that sets them apart from naturally occurring allelic or interspecies variation of the light-activated ion channels of the invention. Modified slow mutant polypeptides generally may exhibit the same qualitative biological activity as their parent light-activated ion channel, although variants can also be selected that have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed modified light-activated ion channel screened for the optimal combination of desired activity. Techniques for making substitution mutations at predetermined sites in DNA having a known sequence are well known, for example, M13 primer mutagenesis and PCR mutagenesis.

In some aspects of the invention, amino acid substitutions may be single residue substitutions; and insertions may be on the order of from 1, 2, 3, 4, 5, 6, 7, up to about 20 amino acids, although larger insertions may be tolerated. Deletions may range from about 1, 2, 3, 4, 5, 6 7, up to about 20 residues, although in some cases deletions may be larger. Substitutions, deletions, insertions or any combination thereof may be used to arrive at a slow mutant polypeptide of the invention. Generally these changes are done on a few amino acids to minimize the alteration of the molecule. However, larger changes may be tolerated in certain circumstances. A modified slow mutant polypeptide of the invention can incorporate unnatural amino acids as well as natural amino acids. An unnatural amino acid can be included in a light-activated ion channel of the invention to enhance a characteristic such as photocurrent, stability, speed, compatibility, open-time, or to lower toxicity, etc. Methods to prepare and functional variants of light-activated molecules are known and practiced in the art.

Variants of slow mutant polypeptides set forth herein that can be used in embodiments of methods of the invention may exhibit the same qualitative light-activated ion channel activity as one or more of the sequences set forth herein, such as SEQ ID Nos: 1, 3, 11, 12, 14, 15, 17, and 18, but may show some altered characteristics such as altered photocurrent, stability, speed, open-time, compatibility, and toxicity, or a combination thereof. For example, the polypeptide can be modified such that it has an increased open-time, results in increased photocurrent and/or has less toxicity than another light-activated ion channel polypeptide.

Another aspect of the invention provides nucleic acid sequences that encode slow mutant polypeptides of the invention. It is understood by those in the art that slow mutant polypeptides of the present invention can be coded for by more than one nucleic acid sequence. Each amino acid in the protein is represented by one or more sets of three nucleic acids (codons). Because many amino acids are represented by more than one codon there is not a unique nucleic acid sequence that codes for a given protein. Those in the art will understand how to make and use a nucleic acid sequence that encodes a slow mutant polypeptide of the invention based on knowledge of the amino acid sequence of the protein. A nucleic acid sequence that codes for a polypeptide is referred to as the "gene" of that polypeptide. A gene can be RNA, DNA, or other nucleic acid than will code for the polypeptide.

It is understood in the art that the codon systems in different organisms can be slightly different, and therefore where the expression of a given protein from a given organism is desired, the nucleic acid sequence can be modified for expression within that organism. Thus, in some embodiments of the invention, a slow mutant polypeptide of the invention is encoded by a mammalian-codon-optimized nucleic acid sequence, which may in some embodiments be a human-codon optimized nucleic acid sequence. An aspect of the invention provides a nucleic acid sequence that encodes a slow mutant polypeptide of the invention that is optimized for expression in a mammalian cell. In some embodiments of the invention, a nucleic acid sequence that encodes a slow mutant polypeptide of the invention includes a nucleic acid sequence optimized for expression in a human cell.

Delivery of Slow Mutant Molecules

Delivery of a slow mutant polypeptide to a cell and/or expression of a slow mutant polypeptide in a cell can be done using art-known delivery means. In some embodiments of the invention a slow mutant polypeptide of the invention is included in a fusion protein. It is well known in the art how to prepare and utilize fusion proteins that comprise a polypeptide sequence. In certain embodiments of the invention, a fusion protein can be used to deliver a slow mutant polypeptide into a cell and in some embodiments a fusion protein can be used to target a slow mutant polypeptide of the invention to specific cells or to specific cells, tissues, or regions in a subject. Targeting and suitable targeting sequences for delivery of a slow mutant polypeptide of the invention into a desired cell, tissue or region can be performed using art-known procedures.

In some embodiments of the invention, a slow mutant light-activated ion channel of the invention is genetically introduced into a cellular membrane, and reagents and methods are provided for genetically targeted expression of slow mutant polypeptides, including but not limited to: SEQ ID Nos: 1, 3, 11, 12, 14, 15, 17, 18, and functional variants of any thereof. Genetic targeting can be used to deliver one or more slow mutant polypeptides to specific cell types, to specific cell subtypes, to specific spatial regions within an organism, and to sub-cellular regions within a cell. Genetic targeting also relates to the control of the amount of a slow mutant polypeptide expressed and the timing of the expression.

Some embodiments of the invention include a reagent for genetically targeted expression of a slow mutant polypeptide, wherein the reagent comprises a vector that contains the gene for the light-activated ion channel polypeptide. As used herein, the term "vector" refers to a polynucleotide molecule capable of transporting between different genetic environments another nucleic acid sequence to which it has been operatively linked. The term "vector" may also refer to a virus or organism that is capable of transporting the polynucleotide molecule. One type of vector is an episome, i.e., a polynucleotide molecule capable of extra-chromosomal replication. Some useful vectors are those capable of autonomous replication and/or expression of nucleic acid sequences to which they are linked. Vectors capable of directing the expression of genes to which they are operatively linked are referred to herein as "expression vectors." Other useful vectors, include, but are not limited to viruses such as lentiviruses, retroviruses, adenoviruses, and phages. Vectors useful in some methods of the invention can genetically insert a slow mutant polypeptide including, but not limited to one set forth herein as: SEQ ID NO: 1, 3, 11, 12, 14, 15, 17, 18, or a functional variant thereof into dividing and non-dividing cells and can insert slow mutant polypeptides into cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. Methods suitable to prepare and use expression vectors, polynucleotide sequences, promoters, delivery agents, labeling agents, etc. to express slow mutant polypeptides of the invention are known in the art.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a light-activated ion channel polypeptide in a wide variety of cell types—thus a promoter for a gene that is widely expressed in a variety of cell types, for example a "housekeeping gene" can be used to express a light-activated ion channel polypeptide in a variety of cell types. Non-limiting examples of general promoters are provided elsewhere herein and suitable alternative promoters are well known in the art. In certain embodiments of the invention, a promoter may be an inducible promoter.

A plasmid construct may be used in some embodiments of the invention, to deliver and/or express a slow mutant polypeptide of the invention and the construct may comprise a slow mutant molecule, and one or more of: an AAV-Adeno-associated virus; a trafficking sequence, a signal sequence, an export sequence, a Syn-synapsin promoter, such as but not limited to SEQ ID NO: 30; an HA-hemagglutinin, such as but not limited to SEQ ID NO: 31, which encodes SEQ ID NO: 32; an SS-signal sequence, such as but not limited to SEQ ID NO: 28, which encodes SEQ ID NO: 29; a truncated MHC class I antigen; an ER2-Endoplasmic reticulum export signal, such as but not limited to SEQ ID NO: 24, which encodes SEQ ID NO: 25; a KGC C terminal export sequence from the potassium channel Kir2.1, such as but not limited to SEQ ID NO: 26, which encodes SEQ ID NO: 27. Additional molecules that can be included in constructs for use in methods of the invention, see for example, Kügler, S. et al., Gene Therapy 10, 337-347, (2003); Niman, H. L. et al., Proc. Natl. Acad. Sci. USA 80:4949-4953 (1983); Gradinaru, V. et al., Brain Cell Biol. 36, 129-139 (2008); and Chow B. Y. et al., Nature, 463, 98-102(2010), the content of each of which is incorporated herein by reference in its entirety.

As used herein, polypeptide components of a fusion protein, such as, but not limited to: a slow mutant polypeptide, a targeting polypeptide, a signal polypeptide, a trafficking polypeptide, a detectable label polypeptide, may be referred to being "fused" to each other. For example, when referring to a slow mutant polypeptide and an targeting polypeptide that are part of a fusion protein, the slow mutant polypeptide may be referred to as being "fused" to the targeting polypeptide. Trafficking polypeptides, export polypeptides, signal polypeptides, targeting polypeptides are known in the art and can be included in a fusion protein to direct the location, (also referred to as: localization), of the expressed polypeptide to a specific cell region of interest such as a membrane etc.

Compositions of the invention may include a slow mutant molecule and one or more additional molecules. In some embodiments of the invention, a slow mutant molecule is a polypeptide. In certain embodiments of the invention, a slow mutant molecule is a polynucleotide with a nucleic acid sequence that encodes a slow mutant polypeptide. In some aspects of the invention, a composition comprising a slow mutant molecule of the invention is a pharmaceutical composition. In some aspects of the invention the pharmaceutical composition comprises a slow mutant polypeptide and/or its encoding nucleic acid and a pharmaceutically acceptable carrier. Additional components that are optionally included in a composition include but are not limited to: one or more: vectors, nucleic acid molecules, polypeptides, detectable labels, carrier molecules, targeting molecules, etc.

Functional variants of other components of vectors and/or fusion proteins are also envisioned, for example functional variants of ER2, SS, hemagglutinin, syn promoters, Kir2 sequences and other export sequences, signal sequences, trafficking sequences etc. that may be include in vectors or fusion proteins of the invention.

Component Molecules of Fusion Protein, Vectors, and Compositions

Molecules that may be included in fusion proteins, vectors, compositions, and pharmaceutical compositions of the invention, and can be expressed in cells in methods of the invention, include but are not limited to one or more of: slow mutant polypeptides, detectable label polypeptides, fluorescent polypeptides, targeting polypeptides, trafficking polypeptides, signal polypeptides, export polypeptides, etc.

Non-limiting examples of detectable label polypeptides that may be included in a fusion protein of that also includes a slow mutant polypeptide of the invention, are: green fluorescent protein (GFP); enhanced green fluorescent protein (EGFP), red fluorescent protein (RFP); yellow fluorescent protein (YFP), tdTomato, mCherry, DsRed, cyan fluorescent protein (CFP); far red fluorescent proteins, etc. In certain aspects of the invention, a fluorescent detectable label polypeptide may be included, for example for tracking purposes, testing, assays, etc. Numerous fluorescent proteins and their encoding nucleic acid sequences are known in the art and routine methods can be used to include such sequences in fusion proteins and vectors, respectively, of the invention.

Non-limiting of examples of additional amino acid sequences that may be included in a fusion protein of the invention are promoter sequences, trafficking sequences, including, but not limited to one or more of the sequences set forth herein as SEQ ID NO: 25, 27, 29, and 32. Additional amino acid sequences that can be included in a fusion protein of the invention are known in the art and can be included and used in compositions and methods of the invention using routine methods.

A vector or fusion protein of the invention may also include a functional variant of a slow mutant molecule of the invention. For example a functional variant of SEQ ID NO: 1, 3, parent molecules including but not limited to one or more of: SEQ ID NO: 1-4, 11, 12, 14, 15, 17, and 18. A functional variant that is included in a vector or a fusion protein of the invention, may have one or more additions, deletions, substitutions, or other modifications to the sequence of its parent sequence and retains a portion, or all, of the function of its parent molecule for which the molecule is included in the vector or fusion protein of the invention.

Methods of Use of Slow Mutant Polypeptides

Slow mutant molecules of the invention are well suited for targeting cells and specifically altering voltage-associated cell activities. In some embodiments of the invention, slow mutant polypeptides of the invention can be utilized to introduce cations into cells, thus activating endogenous signaling pathways (such as calcium dependent signaling), and then drugs are applied that modulate the response of the cell (using a calcium or voltage-sensitive dye). This allows compound and drug screening using light to activate channels of interest, and using light to read out the effects of a compound and/or drug on the channels of interest.

According to certain principles of this invention, slow mutant polypeptides can be activated to introduce cations into cells, thus activating endogenous signaling pathways (such as calcium dependent signaling), and drugs may be applied that modulate the response of the cell (using a calcium or voltage-sensitive dye). Another aspect of the invention is the use of a slow mutant polypeptide to decrease the pH of a cell in which it is expressed. Such a technique may be used to treat alkalosis. Another aspect of the invention includes methods of using slow mutant polypeptides to generate sub-cellular voltage or pH gradients, for example, though not limited to, at synapses and in synaptic vesicles to alter synaptic transmission, and mitochondria to improve ATP synthesis.

Working operation of prototypes of this invention have been prepared including genetically expressing slow mutant polypeptides of the invention in excitable cells, illuminating the cells with suitable wavelengths of light, and demonstrating rapid depolarization of the cells in response to the light, as well as slow channel closing and slow release from depolarization upon cessation of light. Depending on the particular implementation, methods of the invention allow light control of cellular functions in vivo, in vitro, or ex vivo. In non-limiting examples of methods of the invention, slow mutant polypeptides of the invention have been expressed in cells in human-optimized form allow depolarization at wavelengths described herein, and have shown extended open-times as described versus corresponding non-slow mutant polypeptides under similar conditions.

Cells and Subjects

A cell used in methods and with sequences of the invention may be an excitable cell or a non-excitable cell. Cell types in which a slow mutant polypeptide of the invention may be expressed and may be used in methods of the invention include prokaryotic and eukaryotic cells. Useful cells include but are not limited to mammalian cells. Examples of cells in which a slow mutant polypeptide of the invention may be expressed are excitable cells, which include cells able to produce and respond to electrical signals. Examples of excitable cell types include, but are not limited to neurons, muscles, cardiac cells, and secretory cells (such as pancreatic cells, adrenal medulla cells, pituitary cells, immune system cells, etc.).

Non-limiting examples of cells that may be used in methods of the invention include: neuronal cells, nervous system cells, cardiac cells, circulatory system cells, immune system cells, visual system cells, auditory system cells, secretory cells, endocrine cells, and muscle cells. In some embodiments, a cell in which a slow mutant polypeptide is expressed and that is used in conjunction with a method of the invention may be a healthy normal cell, which is not known to have a disease, disorder or abnormal condition. In some embodiments, a cell used in conjunction with methods and channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Slow mutant polypeptides of the invention may be expressed in cells in or from culture, cells in solution, cells obtained from subjects, and/or cells in a subject (in vivo cells). Slow mutant polypeptides of the invention may be expressed and activated in cultured cells, cultured tissues (e.g., brain slice preparations, etc.), and in living subjects, etc. As used herein, the term "subject" may refer to, but is not limited to: a human, non-human primate, cow, horse, pig, sheep, goat, dog, cat, rodent, fly or another vertebrate or invertebrate organism.

Controls and Candidate Compound Testing

Slow mutant polypeptides of the invention and methods using slow mutant polypeptides of the invention can be utilized to assess changes in cells, tissues, and subjects in which they are expressed. Some embodiments of the invention include use of slow mutant polypeptides of the invention to identify effects of candidate compounds on cells, tissues, and subjects. Results of testing a slow mutant polypeptide of the invention can be advantageously compared to a control. In some embodiments of the invention one or more slow mutant polypeptides of the invention, non-limiting examples of which are SEQ ID Nos: 1, 3, 11, 12, 14, 15, 17, 18, and functional variants of any thereof, may be expressed in a cell population and used to test the effect of candidate compounds on the cells.

As used herein a control may be a predetermined value, which can take a variety of forms. It can be a single cut-off value, such as a median or mean. It can be established based upon comparative groups, such as cells or tissues that include the slow mutant polypeptide and are contacted with light, but are not contacted with the candidate compound and the same type of cells or tissues that under the same testing condition are contacted with the candidate compound. Another example of comparative groups may include cells or tissues that have a disorder or condition and groups without the disorder or condition. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a slow mutant polypeptide of the invention to identify a candidate therapeutic agent or compound, a slow mutant light-activated ion channel of the invention may be expressed in an excitable cell in culture or in a subject and the excitable cell may be contacted with a light that activates the slow mutant polypeptide channel and with a candidate therapeutic compound. In one embodiment, a test cell that includes a slow mutant polypeptide of the invention can be contacted with a light that depolarizes the cell and also contacted with a candidate compound. The cell, tissue, and/or subject that include the cell can be monitored for the presence or absence of a change that occurs in the test conditions versus the control conditions. For example, in a cell, a change may be a change in the depolarization or in a depolarization-mediated cell characteristic in the test cell versus a control cell, and a change in depolarization or the depolarization-mediated cell characteristic in the test cell compared to the control may indicate that the candidate compound has an effect on the test cell or tissue that includes the cell. In some embodiments of the invention, a depolarization-mediated cell characteristic may be a an action potential, pH change in a cell, release of a neurotransmitter, etc. and may in some embodiments, include a downstream effect on one or more additional cells, which occurs due to the depolarization of the cell that includes the slow mutant polypeptide. Art-known methods can be sued to assess depolarization and depolarization-mediated cell characteristics and changes to the depolarization or depolarization-mediated cell characteristics upon activation of a slow mutant polypeptide channel of the invention, with or without additional contact with a candidate compound.

In some aspects of the invention, a control light-activated ion channel may be a non-slow mutant light-activated ion channel, which in some embodiments of the invention is a non-slow mutant parent polypeptide. For example, a Chronos polypeptide may serve as a control for a slow mutant polypeptide of the invention for which Chronos is its parent. Similarly, a Chrimson, CoChR, CsChr polypeptide may serve as a control for a slow mutant polypeptide of the invention for which a Chrimson, CoChR, CsChr polypeptide, respectively, is the parent.

Candidate-compound identification methods of the invention that are performed in a subject, may include expressing a slow mutant polypeptide in a subject, contacting the subject with a light under suitable conditions to activate the slow mutant polypeptide and depolarize the cell, and administering to the subject a candidate compound. The subject is then monitored to determine whether any change occurs that differs from a control effect in a subject. Thus, for example, a cell in culture can be contacted with a light appropriate to activate a slow mutant polypeptide of the invention in the presence of a candidate compound. A result of such contact with the candidate compound can be measured and compared to a control value as a determination of the presence or absence of an effect of the candidate compound.

Methods of identifying effects of candidate compounds using slow mutant polypeptides of the invention may also include additional steps and assays to further characterize an identified change in the cell, tissue, or subject when the cell is contacted with the candidate compound. In some embodiments, testing in a cell, tissue, or subject can also include one or more cells that has a slow mutant polypeptide of the invention, and that also has one, two, three, or more additional different light-activated ion channels, wherein at least one, two, three, four, or more of additional types of light-activated ion channels are activated by contact with light having a different wavelength than used to activate the slow mutant polypeptide.

In a non-limiting example of a candidate drug identification method of the invention, cells that include a slow mutant polypeptide of the invention are depolarized, thus triggering release of a neurotransmitter from the cell, and then drugs are applied that modulate the response of the cell to depolarization (determined for example using patch clamping methods or other suitable art-known means). Such methods enable compound and drug assays and screening using contact with light under suitable conditions to activate the channels of interest, and using light to read out the effects of the compound or drug on the channels and channel-containing cells of interest. In some embodiments, slow mutant polypeptides of the invention can be used in test systems and assays for assessing membrane protein trafficking and physiological function in heterologously expressed systems and the use of methods to activate slow mutant polypeptides to depolarize a cell or plurality of cells.

Expression and Methods of Use in Cells and Subjects

In some embodiments of the invention, a plurality of one or more slow mutant light-activated channel polypeptides can be used to modify the transmembrane potential (and/or ionic composition) of one or a plurality of cell. For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of a light-activated ion channel of the invention in one, two, three, or more cells in a tissue or organism, can result in depolarization of the single cell or the plurality of cells by contacting the light-activated ion channels with light under suitable conditions to activate the polypeptide and open the channel. As used herein the term "plurality" means more than one.

According to certain aspects of the invention, the performance of a slow mutant molecule or plurality of the same or different slow mutant molecules can be tuned for optimal use, including in the context of their use in conjunction with other light-activated ion channel molecules or optical apparatus. For example, in order to achieve optimal contrast for multiple-color stimulation, one may desire to either improve or decrease the performance of one molecule with respect to one another, by the appendage of trafficking enhancing sequences or creation of genetic variants by site-directed mutagenesis, directed evolution, gene shuffling, or altering codon usage. Slow mutant molecules of the invention and other light-activated ion channel molecules may have inherently varying spectral sensitivity. This may be used to advantage in vivo (where scattering and absorption will vary with respect to wavelength, coherence, and polarization), by tuning the linearity or non-linearity of response to optical illumination with respect to time, power, and illumination history.

Certain embodiments of the invention include expression of 2, 3, 4, or more different types of light-activated ion channel polypeptides, some or all of which are slow mutant polypeptides of the invention, in separate subpopulations of a population of cells, which are referred to herein as "mixed" populations of cells. The subpopulations of cells can be contacted with light in a manner that selectively activates light-activated ion channels in one or more of the subpopulations of cells but not necessarily activating each type of light-activated ion channel in the mixed population. Certain embodiments of the invention include expression of one type of slow mutant light-activated ion channel polypeptide of the invention, in a population of cells, which are referred to herein as "single" populations of cells. In some embodiments of the invention, a single or mixed population of cells is in culture and in certain embodiments of the invention a single or mixed population of cells is in a subject.

Selection of suitable light and contact parameters to optimize the light-activated ion channel open times of slow mutant and non-slow mutant light-activated ion channels in a mixed or single population can be done using routine methods. Single and mixed populations of light activated ion channel polypeptides can be used in methods, assays, and/or treatment methods of the invention. In a mixed population, different light-activated ion channel polypeptides can be independently activated by contacting the light-activated ion channel polypeptides with different activating light parameters that are specific to each type of light-activated ion channel polypeptide.

A non-limiting example of a process to prepare and use a multi-light activated population of cells is as follows. A first light-activated ion channel polypeptide that is a slow mutant polypeptide comprising an amino acid sequence set forth as SEQ ID NO: 1 is expressed in a first subpopulation of a population of cells. A second light-activated ion channel that is not the slow mutant polypeptide is expressed in a second subpopulation of the population of cells, wherein the first and second subpopulations may be non-overlapping subpopulations or may be overlapping subpopulations. The first light-activated ion channel and the second light activated ion channel have ranges of activating light wavelengths that do not entirely overlap. The population of cells is contacted with a light under suitable conditions to activate the first light-activated ion channel polypeptides, for example: appropriate doses of light, wavelength, pulse width, and power that activate the first subpopulation of cells, and the transmembrane voltage deflection is measured in a cell of the second subpopulation of cells contacted with the first light test doses. The first light test dose parameters that results in activation of the first light activated ion channel polypeptides and results in minimal (little or no) sub-threshold transmembrane voltage deflection in the second subpopulation of cells is determined. A similar process is used to identify suitable light dose parameters (such as: of light wavelength, pulse width, and power) that activate the second light-activated ion channels in the second sub population of cells but result in minimal (little or no) sub-threshold transmembrane voltage deflection in the first sub-population of cells. Assays can be performed using such a population of cells, including embodiments of methods in which the population of cells is contacted with the first light test dose and the second light test dose determined using the steps above. The above-described process of optimizing light dose parameters for multi-light activated ion channels, including but not limited to slow mutant polypeptides, can be used to design and implement assays that include slow mutant polypeptides of the invention, as well as other light-activated ion channels that are known in the art.

Treatment Methods

Some aspects of the invention include methods of treating a disorder or condition in a cell, tissue, or subject using one or more slow mutant polypeptides of the invention. Treatment methods of the invention may include administering to a subject in need of such treatment, a therapeutically effective amount of a slow mutant molecule of the invention to treat the disorder. It will be understood that in some aspects of the invention, a treatment administered to a subject is a prophylactic treatment, and in certain aspects of the invention a treatment is administered to a subject following diagnosis of a disease or condition in the subject. A treatment method of the invention may reduce or eliminate a symptom or characteristic of a disorder, disease, or condition in a subject or may eliminate the disorder, disease, or condition itself in the subject. It will be understood that a treatment of the invention may reduce or eliminate progression of a disease, disorder or condition and may in some instances result in the regression of the disease, disorder, or condition in a subject. A treatment need not entirely eliminate the disease, disorder, or condition to be effective. In some embodiments of the invention one or more slow mutant polypeptides of the invention, non-limiting examples of which are SEQ ID Nos: 1, 3, 11, 12, 14, 15, 17, 18, and functional variants thereof, may be expressed in a cell population and used in methods to treat a disorder or condition.

Administration of a slow mutant polypeptide of the invention maybe performed using various art-known methods. In some embodiments of the invention, a vector that encodes a fusion protein comprising a slow mutant polypeptide of an invention is administered to a cell and/or subject, resulting in the presence of the slow mutant polypeptide in a cell in the subject. In certain aspects of the invention, a fusion protein comprising a slow mutant polypeptide of the invention is administered to a cell and/or subject, resulting in the presence of the slow mutant polypeptide in a cell in the subject. In some embodiments of the invention a cell comprising a slow mutant polypeptide or its encoding nucleic acid is administered to a cell and/or subject, resulting in the presence of an expressed slow mutant polypeptide in a cell in the subject. In some aspects of the invention, a slow mutant polypeptide of the invention or its encoding nucleic acid is administered as part of a pharmaceutical composition. A pharmaceutical composition that comprises one or more of a vector comprising a nucleic acid that encodes a slow mutant polypeptide of the invention; a fusion protein comprising a slow mutant polypeptide of the invention; or a cell that comprises a slow mutant polypeptide of the invention or its encoding nucleic acid of the invention, may be administered in embodiments of methods of the invention.

An effective amount of a slow mutant polypeptide or its encoding nucleic acid is an amount that increases the level of the slow mutant polypeptide in a cell, tissue, or subject to a level that is beneficial for the subject. An effective amount may also be determined by assessing physiological effects of administration on a cell or subject, such as a decrease in symptoms of a disease or condition following administration. Art-known assays can also be employed to determine a level of a response to a treatment of the invention. The amount of a treatment may be varied for example by increasing or decreasing the amount of the slow mutant polypeptide or encoding nucleic acid that is administered; by changing the therapeutic composition in which the slow mutant polypeptide or its encoding nucleic acid is administered, by changing the route of administration, by changing the dosage timing, by changing the activation amounts and parameters of a slow mutant polypeptide of the invention, and so on.

An effective amount of a slow mutant molecule for use in methods of the invention, will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the slow mutant polypeptide is to be expressed. An effective amount may also depend on the location of the tissue to be treated. These factors are well known and routinely determined for other therapeutic compounds, including previously known light-activated ion channel molecules by those in the art and can be assessed the used to adjust treatment methods and administration of a slow mutant molecule of the invention with no more than routine experimentation. In some aspects of the invention a maximum dose of a composition to increase the level of a slow mutant polypeptide of the invention, and/or to alter the length or timing of activation of a slow mutant polypeptide of the invention in a subject (alone or in combination with other therapeutic agents) be used, that is, the highest safe dose or amount according to sound medical judgment. It will be understood by those in the art, however, that a patient/subject may insist upon a lower dose or tolerable dose for medical reasons, psychological reasons or for virtually any other reasons.

A slow mutant polypeptide of the invention, such as but not limited to: SEQ ID NO: 1, 3, 11, 12, 14, 15, 17, 18, a functional variant of any thereof, or its encoding nucleic acid may be administered using art-known methods and may be administered as part of a pharmaceutical composition. Pharmaceutical compositions that can be used to administer a slow mutant polypeptide of the invention or its encoding nucleic acid may be administered alone, in combination with each other, and/or in combination with other drug therapies, or other treatment regimens that are administered to subjects. A pharmaceutical composition used in some embodiments of methods of the invention comprise an effective amount of a slow mutant molecule of the invention that will increase the level of the slow mutant polypeptide to a level that produces the desired response in a unit of weight or volume suitable for administration to a subject.

The dose of a pharmaceutical composition that is administered to a subject to increase the level of a slow mutant polypeptide in a cell and/or plurality of cells in the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different and/or more localized delivery route) may be employed to the extent that patient tolerance permits. The amount and timing of activation of a slow mutant polypeptide of the invention (e.g., light wavelength, length of light contact, etc.) that has been administered to a subject can also be adjusted based on efficacy of the treatment in a particular subject. Parameters for illumination and activation of a slow mutant polypeptide of the invention that has been administered to a subject can be determined using information provided herein in conjunction with art-known methods and without requiring undue experimentation.

Various modes of administration will be known to one of ordinary skill in the art that can be used to effectively deliver a pharmaceutical composition to a subject to increase the level of a slow mutant polypeptide of the invention in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular and intradermal administration. Delivery methods may include, but are not limited to injection, microinjection, etc. The invention is not limited by the particular modes of administration disclosed herein. Standard references in the art (e.g., Remington: The Science and Practice of Pharmacy, volumes I & II. Twenty-second edition, L. V. Allen, Jr, editor, Philadelphia, Pa.: Pharmaceutical Press. 2012) provide modes of administration and formulations for delivery of various pharmaceutical preparations and formulations in pharmaceutical carriers and means therein can be used in embodiments of methods of the invention. Other art-known protocols may be used methods to administer a slow mutant molecule of the invention, and in some embodiments of the invention, the dose amount, schedule of administration, sites of administration, mode of administration (e.g., intra-organ) and the like may vary from those presented herein.

Administration of a cell, vector, and/or slow mutant molecule of the invention to increase a level of a slow mutant polypeptide of the invention in an animal other than a human, and administration and use of one or more slow mutant polypeptides of the invention for testing purposes, veterinary therapeutic purposes, or other purposes in non-human animals may be carried out under substantially the same conditions as described above. It will be understood by one of ordinary skill in the art that this invention is applicable to both human and animals. Thus, embodiments of the invention are contemplated for use in animal husbandry and veterinary medicine as well as in human therapeutics.

In some aspects of the invention, methods of treatment comprising use of a slow mutant polypeptide of the invention are applied to cells including but not limited to a neuronal cell, a nervous system cell, a neuron, a cardiac cell, a circulatory system cell, a visual system cell, an auditory system cell, a muscle cell, an immune system cell, an endocrine cell, etc.

Disorders, Diseases and Conditions

Slow mutant polypeptides of the invention may be expressed in predetermined, preselected cell types, and activated to alter voltage-associated cell activities. In some aspects of the invention, a slow mutant polypeptide of the invention may be used to decrease the pH of a cell in which it is expressed. Such a technique may be used to treat alkalosis in a subject. Another aspect of the invention includes expressing a slow mutant polypeptide of the invention in cell membrane and then activating the slow mutant polypeptide and generating sub-cellular voltage or pH gradients, particularly at synapses and in synaptic vesicles to alter synaptic transmission, and mitochondria to improve ATP synthesis.

In some embodiments, methods and slow mutants of the invention may be used for the treatment of visual system disorders, for example to treat vision reduction or loss and to increase visual function and ability in a subject. In a non-limiting example, a treatment method of the invention may include administering a slow mutant polypeptide of the invention to a subject known to have vision reduction or loss, and when expressed in a cell in in the subject the slow mutant polypeptide functions as a light-sensitive cell in the visual system, thereby permitting a gain of visual function in the subject. Other treatment methods are also included in the invention, such as, but not limited to, increasing auditory function in a subject, increasing memory function in a subject, reduction of one or more symptoms of a disease or disorder in a subject treated with one or more methods of the invention.

The present invention in some aspects, includes preparing nucleic acid sequences that encode slow mutant polypeptides of the invention, expressing the polypeptides encoded by the prepared nucleic acid sequences in cells and membranes; illuminating the cells and/or membranes with light under suitable conditions to activate the slow mutant polypeptides, and producing rapid depolarization of the cells and/or a change in conductance across the membrane in response to the light, an extended open-time of the ion channel of the slow mutant polypeptide after activation, versus a non-slow mutant parent light-activated ion channel. In some aspects of the invention the cells and/or membranes are in a subject. The ability to controllably alter voltage across membranes and cell depolarization with light has been demonstrated as has the extended open-time that is a characteristic of the slow mutant polypeptides of the invention. The present invention provides novel ion channel polypeptides that provide longer open-times and can be used in methods of light-control of cellular functions in in vivo, in vitro, or ex vivo. Slow mutant polypeptides of the invention can be activated with lower amounts of light for activation of cells in which they are expressed than are useful in their non-mutant parent light activated ion channel polypeptides and thus their use may be less damaging to cells and tissues in subjects and can also be used in a range of methods for drug screening, treatments, and research applications, some of which are describe herein.

In illustrative implementations of this invention, the ability to optically perturb, modify, or control cellular function offers many advantages than is possible using previously known light-activated ion channel polypeptides and their encoding nucleic acids. The present invention provides slow mutant polypeptides that when contacted with light under suitable conditions: activate rapidly and maintain extended open-time. Slow mutant polypeptides of the invention are deliverable into cells and subjects using routine methods and can be activated using levels of light that minimize cell and tissue damage from light. The reagents use in the present invention (and the class of molecules that they represent), allow, at least: currents activated by light wavelengths not useful in previous light-activated ion channels, light activated ion channels that when activated, permit effectively zero calcium conductance, and different spectra from older molecules (opening up multi-color control of cells).

Non-limiting examples of disorders and conditions that can be treated using methods and slow mutant molecules of the invention include injury, brain damage, immune system conditions, cardiac conditions, cardiac damage, muscle damage, muscle conditions, neurological conditions, degenerative neurological conditions, seizures, vision loss, hearing loss, etc. Diseases and conditions that may be treated using methods and slow mutants of the invention (for example those listed herein) comprise diseases and conditions characterized by abnormal electrical activity in one or more cells. Methods and slow mutant polypeptides of the invention can be expressed in such cells, for example in a subject having the disease or condition, and illuminated with light under suitable conditions in a manner that alters and corrects abnormal electrical activity in the cell or cells.

Non-limiting examples of neurological conditions include memory loss, memory disruption, learning disorders, depression, anxiety, seizure disorders, etc. Non-limiting examples of degenerative neurological conditions include Parkinson's disease, Amyotrophic Lateral Sclerosis (ALS), Alzheimer's disease, etc.

EXAMPLES

Example 1

Preparation and Testing of Single and Double Slow Mutant Polypeptides.

Embodiments of slow mutant molecules were prepared and tested. Results demonstrated that the prepared embodiments of slow mutants resulted in slowing of photo-current decay after a brief activation with light.

Material and Methods

Whole-cell patch-clamp recordings were made using Multiclamp 700B amplifier, a Digidata 1550A digitizer, and a PC running pClamp (Molecular Devices). For in vitro voltage clamp recordings, HEK cells were patched 1 day post transfection and bathed in Tyrode solution containing (in mM) 125 NaCl, 2 KCl, 3 $CaCl_2$, 1 $MgCl_2$, 10 HEPES, 30 glucose, and with pH 7.3. Borosilicate glass pipettes (Warner Instruments) with an outer diameter of 1.2 mm and a wall thickness of 0.255 mm were pulled to a resistance of 3-7 MΩ with a P-97 Flaming/Brown micropipette puller (Sutter Instruments) and filled with a solution containing (in mM) 135 K-gluconate, 8 NaCl, 0.1 $CaCl_2$, 0.6 $MgCl_2$, 1 EGTA, 10 HEPES, 4 Mg-ATP, and 0.4 Na-GTP, and with pH 7.3 and 290 mOsm. Cells were voltage clamped at −65 mV and illuminated by a 470 nm LED (Lumencore) at 17.44 $mW/mm^2$ for 5 ms for photo-stimulation. Data were analyzed using Clampfit (Molecular Devices) and Igor Pro (Wavemetrics).

Results

Figure 2A:
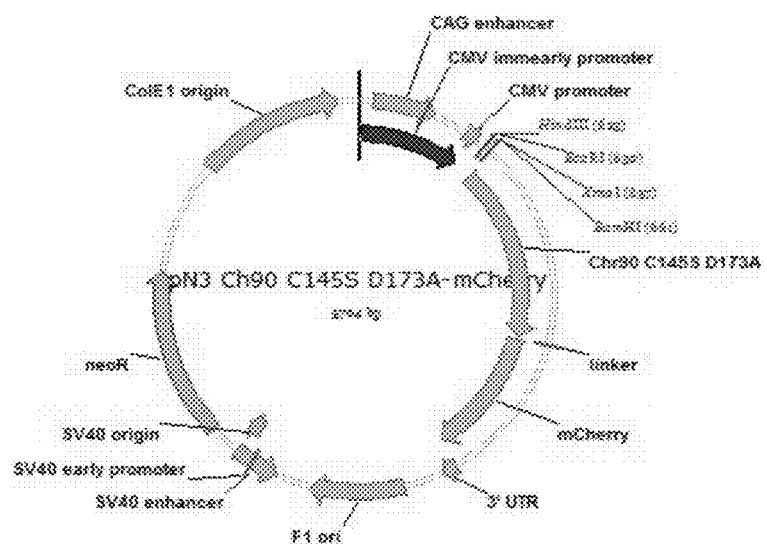
FIG. 2A-C provides schematic diagrams of certain materials used to prepare embodiments of Chronos single and double slow mutants.
Figure 2B:
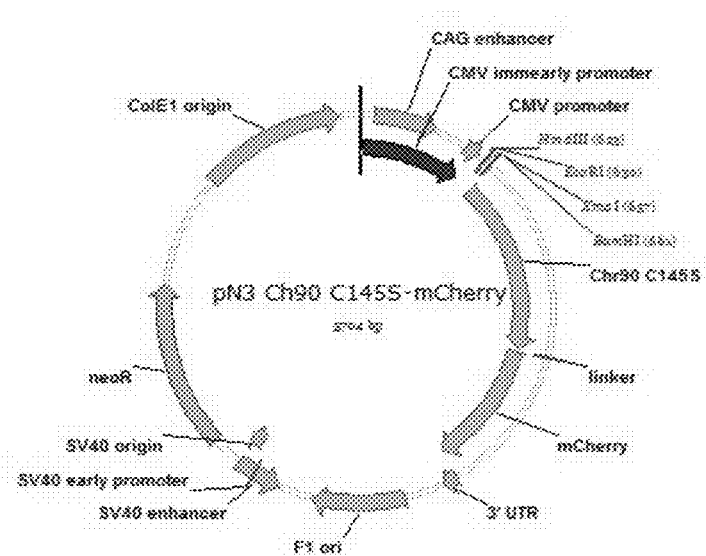
Figure 2C:
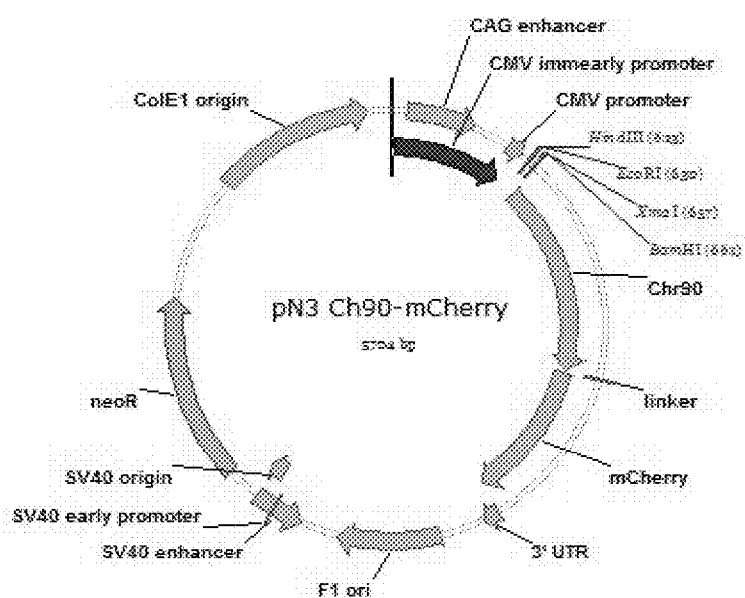
Figure 3A:
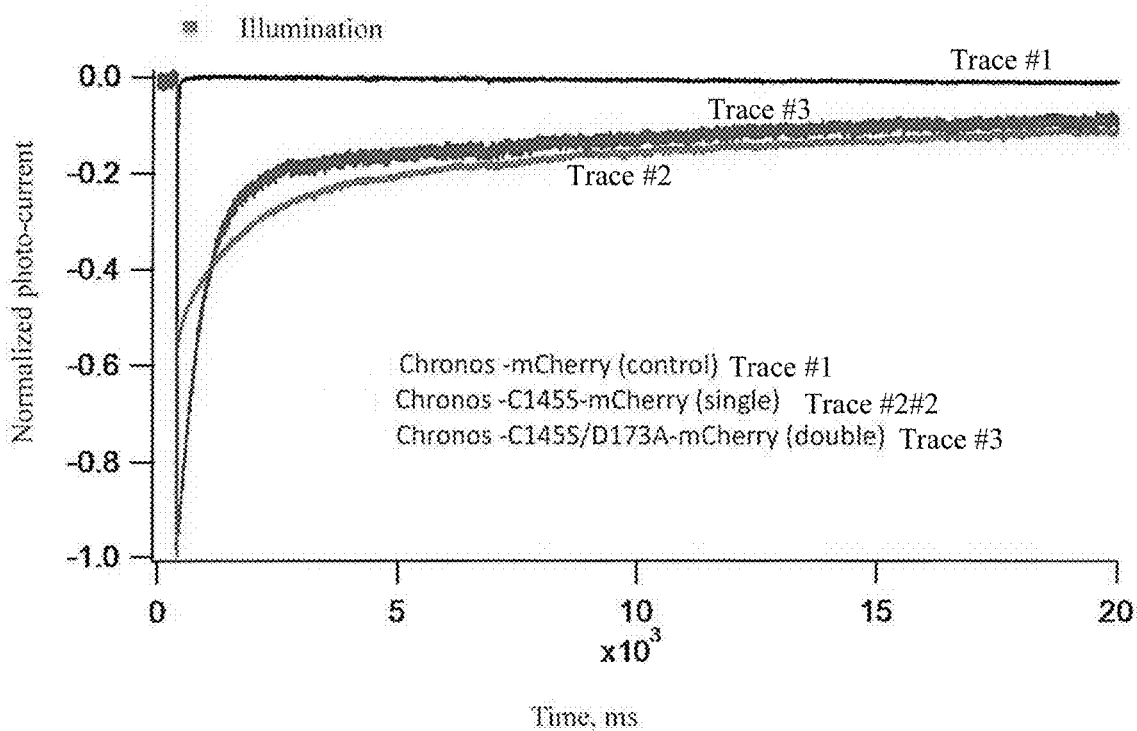
FIG. 3A-B shows recorded traces generated by contacting expressed light-activated ion channel polypeptides with illumination 470 nm at 5 ms.
Figure 3B:
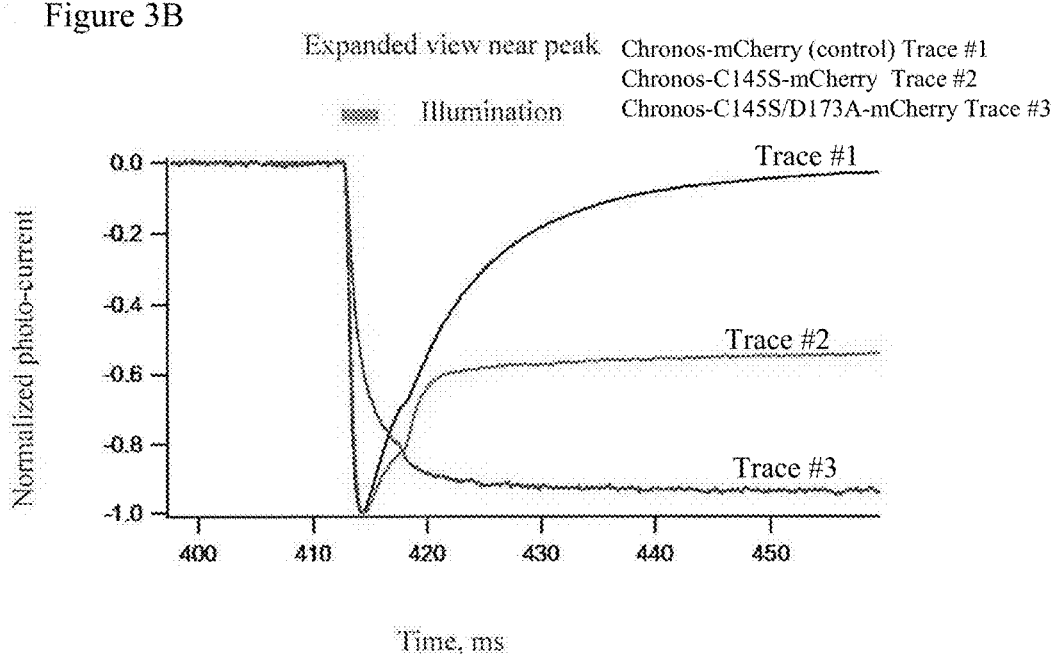

Two Chronos step function mutants were generated (FIGS. 2B and C). Chronos and two Chronos mutants (single mutant having Chronos sequence with a C145S substitution and double mutant having Chronos sequence with C145S and D173A substitutions) were expressed in HEK cells, and then resulting photo-currents produced by 470 nm light illumination were examined. Photo-currents were normalized to peak current amplitude for comparison of channel kinetics. Normalized photo-currents were averaged from 3-4 cells each for Chronos and two mutants (FIG. 3A). As expected Chronos (control) had fastest decay of photo-current following 5 m photo-illumination compare to the mutants (FIG. 3A). Single mutant photo-current initially had faster decay than double mutant but its decay relaxed to similar to that of double mutant about 3 ms post illumination. Interestingly, a close-up examination of peak currents (FIG. 3B) revealed that photo-current activation was also significantly slowed in the double mutant compare to Chronos and the single mutant.

Single (Chronos sequence with a C145S substitution) and double (Chronos sequence with C145S and D173A substitutions) mutations were introduced into a chronos polypeptide and the impact on activity of the expressed polypeptide was determined. The single and double mutations altered the activity of Chronos, which resulted in slowing photo-current decay with a brief photo-activation. Such manipulations can be used in testing and assessing neuron and excitable cell activity in disease, normal cells, in response to contact with compounds or under other conditions.

Example 2

Studies were performed that include preparing sequences and expressing slow mutant polypeptides in cells, tissues, and subjects. The expressed slow mutant polypeptides were selected from slow mutant polypeptides set forth herein as: SEQ ID No: 1, 3, 11, 12, 14, 15, 17, 18 and functional variants thereof. Some of the methods used in the studies are set forth Example 1 and others were routine methods in the art for preparing vectors, expressing fusion proteins, activating light-activated ion channel polypeptides, measuring activity of light-activated ion channel polypeptides, etc. General methods also applicable to light-activated channel molecules and methods used in studies of slow mutant molecules of the invention are disclosed in publications such as US Published Application No. 2010/0234273, US Published Application No. 20110165681, Chow B Y, et al., Methods Enzymol. 2011; 497:425-43; Chow, B Y, et al. Nature 2010 Jan. 7; 463(7277):98-102, the content of each of which is incorporated by reference herein.

Studies were performed to prepare sequences and to express slow mutant polypeptides in cells, tissues, and subjects. Non-limiting exemplary methods are set forth below. Vectors encoding slow mutant polypeptide molecules were prepared using methods described in Example 1 and routine methods were used to deliver the vectors into cells. Fusion proteins that were expressed comprised a slow mutant polypeptide such as one set forth as SEQ ID NO: 1, SEQ ID NO: 3, SEQ ID NO: 11, SEQ ID NO: 12, SEQ ID NO: 14, SEQ ID NO: 15, SEQ ID NO: 17, SEQ ID NO: 18, or a functional variant of any of SEQ ID NO: 1, 3, 11, 12, 14, 15, 17, or 18, or a slow mutant polypeptide described elsewhere herein.

The slow mutant fusion proteins were expressed in one or more in vivo or in vitro cells. A cell in which the fusion protein was expressed was contacted with suitable light to activate the expressed slow mutant polypeptide and alter the electrical activity of the cell in which it was expressed. The activation of the expressed slow mutant polypeptide altered the electrical activity of the cell and in cells with abnormal electrical activity, the activation reduced the abnormal electrical activity of the cell.

Example 3

Experiments are performed in which sequences are prepared and used to express slow mutant polypeptides in cells, tissues, and subjects. Certain of the expressed slow mutant polypeptides are slow mutant polypeptides set forth herein as SEQ ID No: 1, 3, 11, 12, 14, 15, 17, 18 and functional variants thereof. Some of the methods used in the studies are set forth Examples 1 and 2 and others are methods routinely used in the art to prepare vectors, express fusion proteins, activate light-activated ion channel polypeptides, measure activity of light-activated ion channel polypeptides, etc. General methods also applicable to light-activated channel molecules and methods that are used in studies of slow mutant molecules of the invention are disclosed in publications such as US Published Application No. 2010/0234273, US Published Application No. 20110165681, Chow B Y, et al., Methods Enzymol. 2011; 497:425-43; Chow, B Y, et al. Nature 2010 Jan. 7; 463(7277):98-102, the content of each of which is incorporated by reference herein.

Slow mutant sequences are prepared and slow mutant polypeptides are expressed in cells, tissues, and subjects. Some studies are set forth below. Slow mutant polypeptide molecules are prepared using methods described in Examples 1 and 2 and with routine methods. Experiments include expressing fusion proteins comprising a slow mutant polypeptide such as one set forth as SEQ ID NO: 1, SEQ ID NO: 3, SEQ ID NO: 11, SEQ ID NO: 12, SEQ ID NO: 14, SEQ ID NO: 15, SEQ ID NO: 17, SEQ ID NO: 18, or a functional variant of any of SEQ ID NO: 1, 3, 11, 12, 14, 15, 17, or 18 as described elsewhere herein. Vectors are prepared that comprise a nucleic acid sequence that encodes one of SEQ ID NO: 1, 3, 11, 12, 14, 15, 17, 18 or a functional variant thereof. Some of the vectors also include nucleic acids encoding one or more other polypeptides described herein, such as but not limited to a trafficking polypeptide, an export polypeptide, a targeting polypeptide, etc.

Standard administration procedures are used to deliver vectors to cells and subjects, the prepared vector is administered to a human or animal subject who has a disease or condition, or is at risk of a disease or condition, or is suspected of having a disease or condition that includes abnormal electrical activity in one or more cells or regions in the subject.

The slow mutant fusion protein is expressed in a cell in the subject in a cell or region with abnormal electrical activity, the cell in which the fusion protein is expressed is contacted with suitable light to activate the expressed slow mutant polypeptide and alter the electrical activity of the cell in which it is expressed. The altered electrical activity of the cell reduces the abnormal electrical activity of the cell. A disease in the subject that results from the abnormal electrical activity is treated by contacting the expressed fusion protein with suitable light.

Procedures are performed in which a described vector is administered to a subject having blindness and/or visual impairment that at least in part, is the result of abnormal electrical activity in one or more of a neuronal cell and a visual system cell in the subject. Activation of the slow mutant polypeptide that is expressed treats and reduces the blindness in the subject. One or more of the symptoms and/or characteristics of the blindness and/or visual impairment being treated with the procedure is reduced in response to the procedure.

Procedures are performed in which a described vector, prepared using methods set forth in example 1, example 2, and/or using routine procedures. The vector is administered to a subject having hearing loss or hearing impairment that results at least in part from abnormal electrical activity in one or more of a neuronal cell and a auditory system cell in the subject. Activation of the slow mutant polypeptide that is expressed treats one or more symptoms of hearing loss and/or hearing impairment and increases auditory function in the subject. One or more of the symptoms and/or characteristics of the hearing loss and/or hearing impairment being treated with the procedure are reduced in response to the procedure.

Additional procedures are performed in which a described vector is administered to a subject having a seizure disorder or condition that results at least in part from abnormal electrical activity in one or more of a neuronal cell in the brain of the subject. Activation of the slow mutant polypeptide that is expressed treats one or more symptoms of seizure and reduces the seizures in the subject. One or more of the symptoms and/or characteristics of the seizure disorder being treated with the procedure are reduced in response to the procedure.

Procedures are performed in which a described vector is administered to a subject having dementia, memory loss, Parkinson's disease, depression, ALS, and/or Alzheimer's disease symptoms that result at least in part from abnormal electrical activity in one or more of a neuronal cell in the brain in the subject. The slow mutant polypeptide that is expressed is contacted with suitable light in an amount effective to decrease the abnormal electrical activity in the patient's cells that include the fusion protein and treats the dementia, memory loss, Alzheimer's disease, depression, Parkinson's disease, or ALS, and reduces one or more symptoms and/or characteristics of the dementia, memory loss, Alzheimer's disease, depression, and Parkinson's disease, respectively, in the subject. One or more of the symptoms and/or characteristics of the dementia, memory loss, Alzheimer's disease, depression, ALS, and/or Parkinson's disease being treated with the procedure are reduced in response to the procedure.

Procedures are performed in which a described vector is administered to a subject having a cardiac condition that results at least in part from abnormal electrical activity in one or more of a cardiac cell, a neuronal cell, and a muscle cell in the subject. The slow mutant polypeptide that is expressed is contacted with suitable light in an amount effective to reduce the abnormal electrical activity in the patient's cells that include the fusion protein and to treat the cardiac condition and to reduce one or more symptoms and/or characteristics of the cardiac condition in the subject. One or more of the symptoms and/or characteristics of the cardiac condition are reduced in response to the procedure.

Procedures are performed in which a described vector is administered to a subject having an immune system condition that results at least in part from abnormal electrical activity in one or more of an immune system cell in the subject. The slow mutant polypeptide that is expressed is contacted with suitable light in an amount effective to reduce the abnormal electrical activity in the patient's cells that include the fusion protein and to treat the immune system condition and to reduce one or more symptoms and/or characteristics of the immune system condition in the subject. One or more of the symptoms and/or characteristics of the immune system condition are reduced in response to the procedure.

Procedures are performed in which a described vector is administered to a subject having a muscle defect, abnormal muscle activity, muscle associated disease or condition that results at least in part from abnormal electrical activity in a muscle cell in the subject or in a cell that stimulates a muscle cell in the subject. The slow mutant polypeptide that is expressed is contacted with suitable light in an amount effective to reduce the abnormal electrical activity in the patient's cells that include the fusion protein and to treat the muscle defect, abnormal muscle activity, muscle associated disease or condition and to reduce one or more symptoms and/or characteristics of the muscle defect, abnormal muscle activity, muscle associated disease or condition that results from abnormal electrical activity in cells in the subject. One or more of the symptoms and/or characteristics of the muscle defect, abnormal muscle activity, muscle associated disease or condition that results from abnormal electrical activity in cells in the subject are reduced in response to the procedure.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein.

In addition, any combination of two or more such features, systems, articles, materials, and/or methods, if such features, systems, articles, materials, and/or methods are not mutually inconsistent, is included within the scope of the present invention. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated by reference in their entirety herein. It is to be understood that the methods and compositions that have been described above are illustrative applications of the principles of the invention. Numerous modifications may be made by those skilled in the art without departing from the scope of the invention. Although the invention has been described in detail for the purpose of illustration, it is understood that such detail is solely for that purpose and variations can be made by those skilled in the art without departing from the spirit and scope of the invention, which is defined by the following claims.

What is claimed:

1. (Previously :Presented) A light-activated ion channel polypeptide comprising an amino acid sequence set forth as
   (a) SEQ ID NO: 1, SEQ ID NO: 1 with one or more of substitutions: A18G, A36G, D51E, I68V, A94G, I113L, I113V, R165K, A210G, and I257V; or a functional variant of SEQ ID NO: 1 with Serine (S) amino acid position corresponding to amino acid 145 of SEQ ID NO: 1, and at least 99% sequence identity to amino acids 61-295 of SEQ ID NO: 1 and at least 98% sequence identity to the remaining amino acids in SEQ ID NO: 1;
   (b) SEQ ID NO: 11, SEQ ID NO: 11 with one or more of substitutions: A8G, D29E, D56E, R85K, A101G, A119G, I221L, and I221V; or a functional variant of SEQ ID NO: 11 with S at the amino acid position corresponding to amino acid 170 of SEQ ID NO: 11 and at least 99% sequence identity to SEQ ID NO: 11;
   (c) SEQ ID NO: 12, SEQ ID NO: 12 with one or more of substitutions: A8G, D29E, D56E, R85K, A101G, A119G, I221L, and I221V; or a functional variant of SEQ ID NO: 12 with S and A at the amino acid positions corresponding to amino acids 170 and 198, respectively, of SEQ ID NO: 12 and at least 99% sequence identity to SEQ ID NO: 12;
   (d) SEQ ID NO: 14, SEQ ID NO: 14 with one or more of substitutions: D21E, I44L, I44V, R56K, I75L, I75V, I156L, I156V, and D223E; or a functional variant of SEQ ID NO: 14 with S at the amino acid position corresponding to amino acid 108 of Seq ID NO: 14 and at least 99% sequence identity to SEQ ID NO: 14;
   (e) SEQ ID NO: 15, SEQ ID NO: 15 with one or more of substitutions: D21E, I44L, I44V, R56K, I75L, I75V, I156L, I156V, and D223E; or a functional variant of SEQ ID NO: 15 with S and A at the amino acid positions corresponding to amino acids 108 and 136, respectively of SEQ ID NO: 15 and at least 99% sequence identity to SEQ ID NO: 15;
   (f) SEQ ID NO: 17, SEQ ID NO: 17 with one or more of substitutions: A12G, D50E, A88G, A108G, I126L, I126V, R157K, R246K, and A279G; or a functional variant of SEQ ID NO: 17 with S at the amino acid position corresponding to amino acid 165 of SEQ ID NO: 17 and at least 99% sequence identity to SEQ ID NO: 17; and
   (g) SEQ ID NO: 18, SEQ ID NO: 18 with one or more of substitutions: A12G, D50E, A88G, A108G, I126L, I126V, R157K, R246K, and A279G; or a functional variant of SEQ ID NO: 18 with S and A at the amino acid positions corresponding to amino acids 165 and 193, respectively, of SEQ ID NO: 18 and at least 99% sequence identity to SEQ ID NO: 18.

2. The light-activated ion channel polypeptide of claim 1, wherein the amino acid sequence of the functional variant includes an Alanine (A) at the position of amino acid 173 of SEQ ID NO: 1.

3. The light-activated ion channel polypeptide of claim 1, wherein the light activated ion channel polypeptide is comprises the amino acid sequence set forth as SEQ ID NO: 3.

4. The light-activated ion channel polypeptide of claim 1, wherein activating the ion channel polypeptide opens the ion channel of the light-activated ion channel polypeptide, and wherein the channel remains in an open state for a time period longer than an open state time period of an activated control light-activated ion channel polypeptide, wherein the control light-activated ion channel polypeptide is one of a Chronos polypeptide comprising the amino acid sequence set forth as SEQ ID NO: 6, Chrimson polypeptide comprising the amino acid sequence set forth as SEQ ID NO: 10, a CoChR polypeptide comprising the amino acid sequence set forth as SEQ ID NO: 13, and a CsChR polypeptide comprising the amino acid sequence set forth as SEQ ID NO: 16.

5. A membrane comprising the light-activated ion channel polypeptide of claim 1, wherein optionally the membrane is a cell membrane.

6. A cell comprising the light-activated ion channel polypeptide of claim 1.

7. The cell of claim 6, wherein the cell is an excitable cell.

8. The light-activated ion channel polypeptide of claim 1, wherein activating the light-activated ion channel polypeptide alters the ion conductivity of the membrane in which the light-activated ion channel polypeptide is expressed.

9. A method of altering ion conductivity of a membrane, the method comprising, expressing in a host membrane at least one of a light-activated ion channel polypeptide comprising an amino acid sequence set forth as (a) SEQ ID NO: 1, SEQ ID NO: 1 with one or more of substitutions: A18G, A36G, D51E, I68V, A94G, I113L, I113V, R165K, A210G, and I257V; or a functional variant of SEQ ID NO: 1 with Serine (S) at the amino acid position corresponding to amino acid 145 of SEQ ID NO: 1, and at least 99% sequence identity to amino acids 61-295 of SEQ ID NO: 1 and at least 98% sequence identity to the remaining amino acids in SEQ ID NO: 1;

(b) SEQ ID NO: 11, SEQ ID NO: 11 with one or more of substitutions: A8G, D29E, D56E, R85K, A101G, A119G, I221L, and I221V; or a functional variant of SEQ ID NO: 11 with a S at the amino acid position corresponding to amino acid 170 of SEQ ID NO: 11 and at least 99% sequence identity to SEQ ID NO: 11;

(c) SEQ ID NO: 12, SEQ ID NO: 12 with one or more of substitutions: A8G, D29E, D56E, R85K, A101G, A119G, I221L, and I221V; or a functional variant of SEQ ID NO: 12 with an S and an A at the amino acid positions corresponding to amino acids 170 and 198, respectively, of SEQ ID NO: 12 and at least 99% sequence identity to SEQ ID NO: 12;

(d) SEQ ID NO: 14, SEQ ID NO: 14 with one or more substitutions: D21E, I44L, I44V, R56K, I75L, I75V, I156L, I156V, and D223E; or a functional variant of SEQ ID NO: 14 with an S at the amino acid position corresponding to amino acid 108 of Seq ID NO: 14 and at least 99% sequence identity to SEQ ID NO: 14;

(e) SEQ ID NO: 15, SEQ ID NO: 15 with one or more of substitutions: D21E, I44L, I44V, R56K, I75L, I75V, I156L, I156V, and D223E; or a functional variant of SEQ ID NO: 15 with an S and an A at the amino acid positions corresponding to amino acids 108 and 136, respectively of SEQ ID NO: 15 and at least 99% sequence identity to SEQ ID NO: 15;

(f) SEQ ID ID NO: 17, SEQ ID NO: 17 with one or more of substitutions: A12G, D50E, A88G, A108G, I126L, I126V, R157K, R246K, and A279G; or a functional variant of SEQ ID NO: 17 with an S at the amino acid position corresponding to amino acid 165 of SEQ ID NO: 17 and at least 99% sequence identity to SEQ ID NO: 17; and (g) SEQ ID NO: 18, SEQ ID NO: 18 with one or more of substitutions: A12G, D50E, A88G, A108G, I126L, I126V, R157K, R246K, and A279G; or a functional variant of SEQ ID NO: 18 with S and A at the amino acid positions corresponding to amino acids 165 and 193, respectively, of SEQ ID NO: 18 and at least 99% sequence identity to SEQ ID NO: 18 and contacting the at least one of the expressed light-activated ion channel polypeptides with a light that activates at least one of the light-activated ion channels and alters the ion conductivity of the host membrane.

10. The method of claim 9, wherein the host membrane is a cell membrane.

11. A method of assessing the effect of a candidate compound on ion conductivity of a membrane, the method comprising, (a) contacting a test membrane comprising the light-activated ion channel polypeptide comprising the amino acid sequence set forth as;

(i) SEQ ID NO: 1, SEQ ID NO: 1 with one or more of substitutions: A18G, A36G, D51E, I68V, A94G, I113L, I113V, R165K, A210G, and I257V; or a functional variant of SEQ ID NO: 1 with a Serine (S) amino acid position corresponding to amino acid 145 of SEQ ID NO: 1, and at least 99% sequence identity to amino acids 61-295 of SEQ ID NO: 1 and at least 98% sequence identity to the remaining amino acids in SEQ ID NO: 1;

(ii) SEQ ID NO: 11, SEQ ID NO: 11 with one or more of substitutions: A8G, D29E, D56E, R85K, A101G, A119G, I221L, and I221V; or a functional variant of SEQ ID NO: 11 with S at the amino acid position corresponding to amino acid 170 of SEQ ID NO: 11 and at least 99% sequence identity to SEQ ID NO: 11;

(iii) SEQ ID NO: 12, SEQ ID NO: 12 with one or more of substitutions: A8G, D29E, D56E, R85K, A101G, A119G, I221L, and I221V; or a functional variant of SEQ ID NO: 12 with S and A at the amino acid positions corresponding to amino acids 170 and 198, respectively, of SEQ ID NO: 12 and at least 99% sequence identity to SEQ ID NO: 12;

(iv) SEQ ID NO: 14, SEQ ID NO: 14 with one or more substitutions: D21E, I44L, I44V, R56K, I75L, I75V, I156L, I156V, and D223E; or a functional variant of SEQ ID NO: 14 with S at the amino acid position corresponding to amino acid 108 of Seq ID NO: 14 and at least 99% sequence identity to SEQ ID NO: 14;

(v) SEQ ID NO: 15, SEQ ID NO: 15 with one or more of substitutions: D21E, I44L, I44V, R56K, I75L, I75V, I156L, I156V, and D223E; or a functional variant of SEQ ID NO: 15 with S and A at the amino acid positions corresponding to amino acids 108 and 136, respectively of SEQ ID NO: 15 and at least 99% sequence identity to SEQ ID NO: 15;

(vi) SEQ ID ID NO: 17, SEQ ID NO: 17 with one or more of substitutions: A12G, D50E, A88G, A108G, I126L, I126V, R157K, R246K, and A279G; or a functional variant of SEQ ID NO: 17 with S at the amino acid position corresponding to amino acid 165 of SEQ ID NO: 17 and at least 99% sequence identity to SEQ ID NO: 17; or (vii) SEQ ID NO: 18, SEQ ID NO: 18 with one or more of substitutions: A12G, D50E, A88G, A108G, I126L, I126V, R157K, R246K, and A279G; or a functional variant of SEQ ID NO: 18 with S and A at the amino acid positions corresponding to amino acids 165 and 193, respectively, of SEQ ID NO: 18 and at least 99% sequence identity to SEQ ID NO: 18, with light under conditions suitable for altering ion conductivity of the membrane;

(b) contacting the test membrane with a candidate compound; and (c) identifying the presence or absence of a change in ion conductivity of the membrane contacted with the light and the candidate compound compared to ion conductivity in a control cell contacted with the light and not contacted with the candidate compound; wherein a change in the ion conductivity in the test membrane compared to the control indicates an effect of the candidate compound on the ion conductivity of the test membrane.

12. The method of claim 11, wherein the test membrane is in a test cell.

13. The method of claim 12, wherein altering the ion conductivity of the test membrane depolarizes the test cell.

14. The light-activated ion channel polypeptide of claim 1, wherein
(i) SEQ ID NO: 1 with the one or more substitutions is SEQ ID NO: 1 with A18G; A18G and D51E; A18G, D51E, and I113L; I113L and A210G; or A36G, I113V, A210G, and I257V substitutions;
(ii) SEQ ID NO: 11 with the one or more substitutions is SEQ ID NO: 11 with A8G and D56E; D29E, R85K, A119G, and I221V; A8G, D56E, R85K, A119G, and I221L, or D56E, A119G substitutions;
(iii) SEQ ID NO: 12 with the one or more substitutions is SEQ ID NO: 12 with A8G; A101G; D29E, R85K, and I221V; or A8G, D56E, A101G, A119G, and I221L substitutions;
(iv) SEQ ID NO: 14 with the one or more substitutions is SEQ ID NO: 14 with D21E; I75L and I156V; I44L, R56K, I156L, and D223E; or D21E, I44V, R56K, I75L, and I156V substitutions;
(v) SEQ ID NO: 15 with the one or more substitutions is SEQ ID NO: 15 with D21E; I44V, I75L, I157L, and D223E; D21E, I44L, I75V, I156V, and D223E; or I75V and D223E substitutions;
(vi) SEQ ID NO: 17 with the one or more substitutions is SEQ ID ON: 17 with A12G and A88G; D50E, A12G, A108G, R157K, R246K, and A279G; or I126V and R157K substitutions; and
(vii) SEQ ID NO: 18 with the one or more substitutions is SEQ ID NO: 18 with A12G; A88G and I126L, D50E, A88G, I126V, R157K, and A279G; or I126V and R246K substitutions.

15. The method of claim 9, wherein
(i) SEQ ID NO: 1 with the one or more substitutions is SEQ ID NO: 1 with A18G; A18G and D51E; A18G, D51E, and I113L; I113L and A210G; or A36G, I113V, A210G, and I257V substitutions;
(ii) SEQ ID NO: 11 with the one or more substitutions is SEQ ID NO: 11 with A8G and D56E; D29E, R85K, A119G, and I221V; A8G, D56E, R85K, A119G, and I221L, or D56E, A119G substitutions;
(iii) SEQ ID NO: 12 with the one or more substitutions is SEQ ID NO: 12 with A8G; A101G; D29E, R85K, and I221V; or A8G, D56E, A101G, A119G, and I221L substitutions;
(iv) SEQ ID NO: 14 with the one or more substitutions is SEQ ID NO: 14 with D21E; I75L and I156V; I44L, R56K, I156L, and D223E; or D21E, I44V, R56K, I75L, and I156V substitutions;
(v) SEQ ID NO: 15 with the one or more substitutions is SEQ ID NO: 15 with D21E; I44V, I75L, I157L, and D223E; D21E, I44L, I75V, I156V, and D223E; or I75V and D223E substitutions;
(vi) SEQ ID NO: 17 with the one or more substitutions is SEQ ID ON: 17 with A12G and A88G; D50E, A12G, A108G, R157K, R246K, and A279G; or I126V and R157K substitutions; and
(vii) SEQ ID NO: 18 with the one or more substitutions is SEQ ID NO: 18 with A12G; A88G and I126L, D50E, A88G, I126V, R157K, and A279G; or I126V and R246K substitutions.

16. The method of claim 11, wherein
(i) SEQ ID NO: 1 with the one or more substitutions is SEQ ID NO: 1 with A18G; A18G and D51E; A18G, D51E, and I113L; I113L and A210G; or A36G, I113V, A210G, and I257V substitutions;
(ii) SEQ ID NO: 11 with the one or more substitutions is SEQ ID NO: 11 with A8G and D56E; D29E, R85K, A119G, and I221V; A8G, D56E, R85K, A119G, and I221L, or D56E, A119G substitutions;
(iii) SEQ ID NO: 12 with the one or more substitutions is SEQ ID NO: 12 with A8G; A101G; D29E, R85K, and I221V; or A8G, D56E, A101G, A119G, and I221L substitutions;
(iv) SEQ ID NO: 14 with the one or more substitutions is SEQ ID NO: 14 with D21E; I75L and I156V; I44L, R56K, I156L, and D223E; or D21E, I44V, R56K, I75L, and I156V substitutions;
(v) SEQ ID NO: 15 with the one or more substitutions is SEQ ID NO: 15 with D21E; I44V, I75L, I157L, and D223E; D21E, I44L, I75V, I156V, and D223E; or I75V and D223E substitutions;
(vi) SEQ ID NO: 17 with the one or more substitutions is SEQ ID ON: 17 with A12G and A88G; D50E; A12G, A108G, R157K, R246K, and A279G; or I126V and R157K substitutions; and
(vii) SEQ ID NO: 18 with the one or more substitutions is SEQ ID NO: 18 with A12G; A88G and I126L; D50E, A88G, I126V, R157K, and A279G; or I126V and R246K substitutions.

* * * * *

SEQUENCE LISTING

<160> NUMBER OF SEQ ID NOS: 32

<210> SEQ ID NO 1
<211> LENGTH: 325
<212> TYPE: PRT
<213> ORGANISM: Artificial Sequence
<220> FEATURE:
<223> OTHER INFORMATION: Synthetic polypeptide

<400> SEQUENCE: 1

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Ser Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325

<210> SEQ ID NO 2
<211> LENGTH: 975
<212> TYPE: DNA

<213> ORGANISM: Artificial Sequence
<220> FEATURE:
<223> OTHER INFORMATION: Synthetic oligonucleotide

<400> SEQUENCE: 2

```
atggaaacag ccgccacaat gacccacgcc tttatctcag ccgtgcctag cgccgaagcc      60
acaattagag gcctgctgag cgccgcagca gtggtgacac cagcagcaga cgctcacgga     120
gaaacctcta cgccacaac agccggagcc gatcacggtt gcttcccca catcaaccac       180
ggaaccgagc tgcagcacaa gatcgcagtg ggactccagt ggttcaccgt gatcgtggct     240
atcgtgcagc tcatcttcta cggttggcac agcttcaagg ccacaaccgg ctgggaggag     300
gtctacgtct gcgtgatcga gctcgtcaag tgcttcatcg agctgttcca cgaggtcgac     360
agcccagcca cagtgtacca gaccaacgga ggagccgtga tttggctgcg gtacagcatg     420
tggctcctga ctagccccgt gatcctgatc cacctgagca acctgaccgg actgcacgaa     480
gagtacagca gcggaccat gaccatcctg gtgaccgaca tcggcaacat cgtgtggggg     540
atcacagccg cctttacaaa gggcccctg aagatcctgt tcttcatgat cggcctgttc      600
tacggcgtga cttgcttctt ccagatcgcc aaggtgtata tcgagagcta ccacaccctg     660
cccaaaggcg tctgccggaa gatttgcaag atcatggcct acgtcttctt ctgctcttgg     720
ctgatgttcc ccgtgatgtt catcgccgga cacgagggac tgggcctgat cacaccttac     780
accagcggaa tcgccaccct gatcctggat ctgatcagca gaacacttg gggcttcctg      840
ggccaccacc tgagagtgaa gatccacgag cacatcctga tccacggcga catccggaag    900
acaaccacca tcaacgtggc cggcgagaac atggagatcg agaccttcgt cgacgaggag    960
gaggagggag gagtg                                                     975
```

<210> SEQ ID NO 3
<211> LENGTH: 325
<212> TYPE: PRT
<213> ORGANISM: Artificial Sequence
<220> FEATURE:
<223> OTHER INFORMATION: Synthetic polypeptide

<400> SEQUENCE: 3

```
Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Ser Pro Val Ile Leu Ile His Leu Ser Asn Leu Thr Gly Leu His Glu
145                 150                 155                 160
```

```
Glu Tyr Ser Lys Arg Thr Met Thr Ile Leu Val Thr Ala Ile Gly Asn
                165                 170                 175

Ile Val Trp Gly Ile Thr Ala Ala Phe Thr Lys Gly Pro Leu Lys Ile
            180                 185                 190

Leu Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
                260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
                325

<210> SEQ ID NO 4
<211> LENGTH: 975
<212> TYPE: DNA
<213> ORGANISM: Artificial Sequence
<220> FEATURE:
<223> OTHER INFORMATION: Synthetic oligonucleotide

<400> SEQUENCE: 4
atggaaacag ccgccacaat gacccacgcc tttatctcag ccgtgcctag cgccgaagcc      60
acaattagag gcctgctgag cgccgcagca gtggtgacac cagcagcaga cgctcacgga     120
gaaacctcta cgccacaac agccggagcc gatcacggtt gcttcccca catcaaccac       180 ggaaccgagc tgcagcacaa gatcgcagtg ggactccagt ggttcaccgt gatcgtggct     240
atcgtgcagc tcatcttcta cggttggcac agcttcaagg ccacaaccgg ctgggaggag     300
gtctacgtct gcgtgatcga gctcgtcaag tgcttcatcg agctgttcca cgaggtcgac     360 agccagcca cagtgtacca gaccaacgga ggagccgtga tttggctgcg gtacagcatg      420
tggctcctga ctagccccgt gatcctgatc cacctgagca acctgaccgg actgcacgaa     480
gagtacagca gcggaccat gaccatcctg gtgaccgcaa tcggcaacat cgtgtggggg     540
atcacagccg cctttacaaa gggcccctg aagatcctgt tcttcatgat cggcctgttc      600
tacggcgtga cttgcttctt ccagatcgcc aaggtgtata tcgagagcta ccacaccctg     660
cccaaaggcg tctgccggaa gatttgcaag atcatggcct acgtcttctt ctgctcttgg     720
ctgatgttcc ccgtgatgtt catcgccgga cacgagggac tgggcctgat cacaccttac     780
accagcggaa tcggccacct gatcctggat ctgatcagca gaacacttg ggcttcctg       840 ggccaccacc tgagagtgaa gatccacgag cacatcctga tccacggcga catccggaag     900
acaaccacca tcaacgtggc cggcgagaac atggagatcg agaccttcgt cgacgaggag     960
gaggagggag gagtg                                                      975
```

```
<210> SEQ ID NO 5
<211> LENGTH: 235
<212> TYPE: PRT
<213> ORGANISM: Artificial Sequence
<220> FEATURE:
<223> OTHER INFORMATION: Synthetic polypeptide

<400> SEQUENCE: 5

Gly Thr Glu Leu Gln His Lys Ile Ala Val Gly Leu Gln Trp Phe Thr
1               5                   10                  15

Val Ile Val Ala Ile Val Gln Leu Ile Phe Tyr Gly Trp His Ser Phe
            20                  25                  30

Lys Ala Thr Thr Gly Trp Glu Glu Val Tyr Val Cys Val Ile Glu Leu
        35                  40                  45

Val Lys Cys Phe Ile Glu Leu Phe His Glu Val Asp Ser Pro Ala Thr
50                  55                  60

Val Tyr Gln Thr Asn Gly Gly Ala Val Ile Trp Leu Arg Tyr Ser Met
65                  70                  75                  80

Trp Leu Leu Thr Cys Pro Val Ile Leu Ile His Leu Ser Asn Leu Thr
                85                  90                  95

Gly Leu His Glu Glu Tyr Ser Lys Arg Thr Met Thr Ile Leu Val Thr
            100                 105                 110

Asp Ile Gly Asn Ile Val Trp Gly Ile Thr Ala Ala Phe Thr Lys Gly
        115                 120                 125

Pro Leu Lys Ile Leu Phe Phe Met Ile Gly Leu Phe Tyr Gly Val Thr
    130                 135                 140

Cys Phe Phe Gln Ile Ala Lys Val Tyr Ile Glu Ser Tyr His Thr Leu
145                 150                 155                 160

Pro Lys Gly Val Cys Arg Lys Ile Cys Lys Ile Met Ala Tyr Val Phe
                165                 170                 175

Phe Cys Ser Trp Leu Met Phe Pro Val Met Phe Ile Ala Gly His Glu
            180                 185                 190

Gly Leu Gly Leu Ile Thr Pro Tyr Thr Ser Gly Ile Gly His Leu Ile
        195                 200                 205

Leu Asp Leu Ile Ser Lys Asn Thr Trp Gly Phe Leu Gly His His Leu
    210                 215                 220

Arg Val Lys Ile His Glu His Ile Leu Ile His
225                 230                 235

<210> SEQ ID NO 6
<211> LENGTH: 325
<212> TYPE: PRT
<213> ORGANISM: Artificial Sequence
<220> FEATURE:
<223> OTHER INFORMATION: Synthetic polypeptide

<400> SEQUENCE: 6

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
            20                  25                  30

Thr Pro Ala Ala Asp Ala His Gly Glu Thr Ser Asn Ala Thr Thr Ala
        35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80
```

```
Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
    130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
            325

<210> SEQ ID NO 7
<211> LENGTH: 975
<212> TYPE: DNA
<213> ORGANISM: Artificial Sequence
<220> FEATURE:
<223> OTHER INFORMATION: Synthetic oligonucleotide

<400> SEQUENCE: 7
atggaaacag ccgccacaat gacccacgcc tttatctcag ccgtgcctag cgccgaagcc      60
acaattagag gcctgctgag cgccgcagca gtggtgacac cagcagcaga cgctcacgga     120
gaaacctcta cgccacaac agccggagcc gatcacggtt gcttccccca catcaaccac      180
ggaaccgagc tgcagcacaa gatcgcagtg ggactccagt ggttcaccgt gatcgtggct     240
atcgtgcagc tcatcttcta cggttggcac agcttcaagg ccacaacggg ctgggaggag     300
gtctacgtct gcgtgatcga gctcgtcaag tgcttcatcg agctgttcca cgaggtcgac     360
agcccagcca cagtgtacca gaccaacgga ggagccgtga tttggctgcg gtacagcatg     420
tggctcctga cttgccccgt gatcctgatc cacctgagca acctgaccgg actgcacgaa     480
gagtacagca gcggaccat gaccatcctg tgaccgaca tcggcaacat cgtgtggggg      540
atcacagccg cctttacaaa gggccccctg aagatcctgt tcttcatgat cggcctgttc     600
tacggcgtga cttgcttctt ccagatcgcc aaggtgtata tcgagagcta ccacaccctg     660
```

```
cccaaaggcg tctgccggaa gatttgcaag atcatggcct acgtcttctt ctgctcttgg    720
ctgatgttcc ccgtgatgtt catcgccgga cacgaggac tgggcctgat cacaccttac    780
accagcggaa tcggccacct gatcctggat ctgatcagca agaacacttg gggcttcctg    840
ggccaccacc tgagagtgaa gatccacgag cacatcctga tccacggcga catccggaag    900
acaaccacca tcaacgtggc cggcgagaac atggagatcg agaccttcgt cgacgaggag    960
gaggagggag gagtg                                                    975
```

<210> SEQ ID NO 8
<211> LENGTH: 927
<212> TYPE: DNA
<213> ORGANISM: Artificial Sequence
<220> FEATURE:
<223> OTHER INFORMATION: Synthetic oligonucleotide

<400> SEQUENCE: 8

```
atggactatg gcggcgcttt gtctgccgtc ggacgcgaac ttttgttcgt tactaatcct     60
gtggtggtga acgggtccgt cctggtccct gaggatcaat gttactgtgc cggatggatt    120
gaatctcgcg gcacgaacgg cgctcagacc gcgtcaaatg tcctgcagtg gcttgcagca    180
ggattcagca ttttgctgct gatgttctat gcctaccaaa cctggaaatc tacatgcggc    240
tgggaggaga tctatgtgtg cgccattgaa atggttaagg tgattctcga gttcttttt    300 gagtttaaga atccctctat gctctacctt gccacaggac accgggtgca gtggctgcgc    360
tatgcagagt ggctgctcac ttgtcctgtc atccttatcc acctgagcaa cctcaccggc    420
ctgagcaacg actacagcag gagaaccatg ggactccttg tctcagacat cgggactatc    480 gtgtggggg ctaccagcgc catggcaacc ggctatgtta agtcatctt ctttttgtctt    540 ggattgtgct atggcgcgaa acattttttt cacgccgcca agcatatat cgagggttat    600 catactgtgc caaagggtcg gtgccgccag gtcgtgaccg gcatggcatg gctgttttc    660 gtgagctggg gtatgttccc aattctcttc attttgggc ccgaaggttt tggcgtcctg    720
agcgtctatg gctccaccgt aggtcacacg ttattgatc tgatgagtaa aaattgttgg    780
gggttgttgg gacactacct gcgcgtcctg atccacgagc acatattgat tcacggagat    840
atccgcaaaa ccaccaaact gaacatcggc ggaacggaga tcgaggtcga gactctcgtc    900
gaagacgaag ccgaggccgg agccgtg                                       927
```

<210> SEQ ID NO 9
<211> LENGTH: 309
<212> TYPE: PRT
<213> ORGANISM: Artificial Sequence
<220> FEATURE:
<223> OTHER INFORMATION: Synthetic polypeptide

<400> SEQUENCE: 9

```
Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ala Tyr Gln Thr Trp Lys Ser Thr Cys Gly
65                  70                  75                  80
```

Trp Glu Glu Ile Tyr Val Cys Ala Ile Glu Met Val Lys Val Ile Leu
            85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
            165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
    290                 295                 300

Glu Ala Gly Ala Val
305

<210> SEQ ID NO 10
<211> LENGTH: 350
<212> TYPE: PRT
<213> ORGANISM: Artificial Sequence
<220> FEATURE:
<223> OTHER INFORMATION: Synthetic polypeptide

<400> SEQUENCE: 10

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
            35                  40                  45

Asp Pro Ser Tyr Gly Leu Ser Asp Ala Gly Tyr Gly Tyr Cys Phe Val
    50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
            85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
            115                 120                 125

```
Cys Cys Val Glu Val Leu Phe Val Thr Leu Glu Ile Phe Lys Glu Phe
            130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
            210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
            275                 280                 285

Ile Gly His Ser Ile Cys Asp Ile Ile Ala Lys Glu Phe Trp Thr Phe
290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Asp Glu Asp Thr Val
            340                 345                 350

<210> SEQ ID NO 11
<211> LENGTH: 350
<212> TYPE: PRT
<213> ORGANISM: Artificial Sequence
<220> FEATURE:
<223> OTHER INFORMATION: Synthetic polypeptide

<400> SEQUENCE: 11

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
            35                  40                  45

Asp Pro Ser Tyr Gly Leu Ser Asp Ala Gly Tyr Gly Tyr Cys Phe Val
50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
                85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
            115                 120                 125

Cys Cys Val Glu Val Leu Phe Val Thr Leu Glu Ile Phe Lys Glu Phe
            130                 135                 140
```

Ser Ser Pro Ala Thr Val Tyr Leu Ser Thr Gly Asn His Ala Tyr Cys
145                 150                 155                 160

Leu Arg Tyr Phe Glu Trp Leu Leu Ser Ser Pro Val Ile Leu Ile Lys
            165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
            195                 200                 205

Gly Leu Ala Thr Asp Trp Leu Lys Trp Leu Leu Tyr Ile Val Ser Cys
            210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
            245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
            275                 280                 285

Ile Gly His Ser Ile Cys Asp Ile Ile Ala Lys Glu Phe Trp Thr Phe
            290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
            325                 330                 335

Glu Val Glu Glu Phe Val Glu Glu Asp Glu Asp Thr Val
            340                 345                 350

<210> SEQ ID NO 12
<211> LENGTH: 350
<212> TYPE: PRT
<213> ORGANISM: Artificial Sequence
<220> FEATURE:
<223> OTHER INFORMATION: Synthetic polypeptide

<400> SEQUENCE: 12

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
            35                  40                  45

Asp Pro Ser Tyr Gly Leu Ser Asp Ala Gly Tyr Gly Tyr Cys Phe Val
50                  55                  60

Glu Ala Thr Gly Gly Tyr Leu Val Val Gly Val Glu Lys Lys Gln Ala
65                  70                  75                  80

Trp Leu His Ser Arg Gly Thr Pro Gly Glu Lys Ile Gly Ala Gln Val
            85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
            115                 120                 125

Cys Cys Val Glu Val Leu Phe Val Thr Leu Glu Ile Phe Lys Glu Phe
            130                 135                 140

Ser Ser Pro Ala Thr Val Tyr Leu Ser Thr Gly Asn His Ala Tyr Cys
145                 150                 155                 160

-continued

```
Leu Arg Tyr Phe Glu Trp Leu Ser Ser Pro Val Ile Leu Ile Lys
            165                 170                 175

Leu Ser Asn Leu Ser Gly Leu Lys Asn Asp Tyr Ser Lys Arg Thr Met
        180                 185                 190

Gly Leu Ile Val Ser Ala Val Gly Met Ile Val Phe Gly Met Ala Ala
            195                 200                 205

Gly Leu Ala Thr Asp Trp Leu Lys Trp Leu Leu Tyr Ile Val Ser Cys
        210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
            245                 250                 255

Met Ala Tyr Ala Tyr Phe Ala Ser Trp Gly Ser Tyr Pro Ile Leu Trp
        260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
        290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Val
            325                 330                 335

Glu Val Glu Glu Phe Val Glu Glu Glu Asp Glu Asp Thr Val
            340                 345                 350

<210> SEQ ID NO 13
<211> LENGTH: 288
<212> TYPE: PRT
<213> ORGANISM: Artificial Sequence
<220> FEATURE:
<223> OTHER INFORMATION: Synthetic polypeptide

<400> SEQUENCE: 13

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
            85                  90                  95

Gln Trp Leu Arg Tyr Ala Glu Trp Leu Leu Thr Cys Pro Val Ile Leu
        100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
        130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
            165                 170                 175
```

```
Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

<210> SEQ ID NO 14
<211> LENGTH: 288
<212> TYPE: PRT
<213> ORGANISM: Artificial Sequence
<220> FEATURE:
<223> OTHER INFORMATION: Synthetic polypeptide

<400> SEQUENCE: 14

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
    50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Ser Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Asp Val Gly Thr Ile Val Trp Gly Ala
    130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
    210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255
```

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

<210> SEQ ID NO 15
<211> LENGTH: 288
<212> TYPE: PRT
<213> ORGANISM: Artificial Sequence
<220> FEATURE:
<223> OTHER INFORMATION: Synthetic polypeptide

<400> SEQUENCE: 15

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
        35                  40                  45

Phe Tyr Ala Tyr Gln Thr Trp Arg Ala Thr Cys Gly Trp Glu Glu Val
50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Ser Pro Val Ile Leu
            100                 105                 110

Ile His Leu Ser Asn Leu Thr Gly Leu Lys Asp Asp Tyr Ser Lys Arg
        115                 120                 125

Thr Met Arg Leu Leu Val Ser Ala Val Gly Thr Ile Val Trp Gly Ala
130                 135                 140

Thr Ser Ala Met Ser Thr Gly Tyr Val Lys Val Ile Phe Phe Val Leu
145                 150                 155                 160

Gly Cys Ile Tyr Gly Ala Asn Thr Phe Phe His Ala Ala Lys Val Tyr
                165                 170                 175

Ile Glu Ser Tyr His Val Val Pro Lys Gly Arg Pro Arg Thr Val Val
            180                 185                 190

Arg Ile Met Ala Trp Leu Phe Phe Leu Ser Trp Gly Met Phe Pro Val
        195                 200                 205

Leu Phe Val Val Gly Pro Glu Gly Phe Asp Ala Ile Ser Val Tyr Gly
210                 215                 220

Ser Thr Ile Gly His Thr Ile Ile Asp Leu Met Ser Lys Asn Cys Trp
225                 230                 235                 240

Gly Leu Leu Gly His Tyr Leu Arg Val Leu Ile His Gln His Ile Ile
                245                 250                 255

Ile Tyr Gly Asp Ile Arg Lys Lys Thr Lys Ile Asn Val Ala Gly Glu
            260                 265                 270

Glu Met Glu Val Glu Thr Met Val Asp Gln Glu Asp Glu Glu Thr Val
        275                 280                 285

<210> SEQ ID NO 16
<211> LENGTH: 346
<212> TYPE: PRT
<213> ORGANISM: Artificial Sequence
<220> FEATURE:
<223> OTHER INFORMATION: Synthetic polypeptide

<400> SEQUENCE: 16

```
Met Ser Arg Leu Val Ala Ala Ser Trp Leu Leu Ala Leu Leu Leu Cys
1               5                   10                  15

Gly Ile Thr Ser Thr Thr Thr Ala Ser Ser Ala Pro Ala Ala Ser Ser
            20                  25                  30

Thr Asp Gly Thr Ala Ala Ala Val Ser His Tyr Ala Met Asn Gly
        35                  40                  45

Phe Asp Glu Leu Ala Lys Gly Ala Val Pro Glu Asp His Phe Val
50                  55                  60

Cys Gly Pro Ala Asp Lys Cys Tyr Cys Ser Ala Trp Leu His Ser His
65                  70                  75                  80

Gly Ser Lys Glu Glu Lys Thr Ala Phe Thr Val Met Gln Trp Ile Val
                85                  90                  95

Phe Ala Val Cys Ile Ile Ser Leu Leu Phe Tyr Ala Tyr Gln Thr Trp
                100                 105                 110

Arg Ala Thr Cys Gly Trp Glu Glu Val Tyr Val Thr Ile Ile Glu Leu
                115                 120                 125

Val His Val Cys Phe Gly Leu Trp His Glu Val Asp Ser Pro Cys Thr
130                 135                 140

Leu Tyr Leu Ser Thr Gly Asn Met Val Leu Trp Leu Arg Tyr Ala Glu
145                 150                 155                 160

Trp Leu Leu Thr Cys Pro Val Ile Leu Ile His Leu Ser Asn Leu Thr
                165                 170                 175

Gly Met Lys Asn Asp Tyr Asn Lys Arg Thr Met Ala Leu Leu Val Ser
                180                 185                 190

Asp Val Gly Cys Ile Val Trp Gly Thr Thr Ala Ala Leu Ser Thr Asp
                195                 200                 205

Phe Val Lys Ile Ile Phe Phe Phe Leu Gly Leu Leu Tyr Gly Phe Tyr
210                 215                 220

Thr Phe Tyr Ala Ala Lys Ile Tyr Ile Glu Ala Tyr His Thr Val
225                 230                 235                 240

Pro Lys Gly Ile Cys Arg Gln Leu Val Arg Leu Gln Ala Tyr Asp Phe
                245                 250                 255

Phe Phe Thr Trp Ser Met Phe Pro Ile Leu Phe Met Val Gly Pro Glu
                260                 265                 270

Gly Phe Gly Lys Ile Thr Ala Tyr Ser Ser Gly Ile Ala His Glu Val
                275                 280                 285

Cys Asp Leu Leu Ser Lys Asn Leu Trp Gly Leu Met Gly His Phe Ile
290                 295                 300

Arg Val Lys Ile His Glu His Ile Leu Val His Gly Asn Ile Thr Lys
305                 310                 315                 320

Lys Thr Lys Val Asn Val Ala Gly Asp Met Val Glu Leu Asp Thr Tyr
                325                 330                 335

Val Asp Gln Asp Glu Glu His Asp Glu Gly
                340                 345
```

<210> SEQ ID NO 17
<211> LENGTH: 346
<212> TYPE: PRT
<213> ORGANISM: Artificial Sequence
<220> FEATURE:
<223> OTHER INFORMATION: Synthetic polypeptide

<400> SEQUENCE: 17

Met Ser Arg Leu Val Ala Ala Ser Trp Leu Leu Ala Leu Leu Leu Cys

```
          1               5                  10                 15
Gly Ile Thr Ser Thr Thr Thr Ala Ser Ser Ala Pro Ala Ala Ser Ser
              20                 25                 30

Thr Asp Gly Thr Ala Ala Ala Val Ser His Tyr Ala Met Asn Gly
          35                 40                 45

Phe Asp Glu Leu Ala Lys Gly Ala Val Val Pro Glu Asp His Phe Val
      50                 55                 60

Cys Gly Pro Ala Asp Lys Cys Tyr Cys Ser Ala Trp Leu His Ser His
65                 70                 75                 80

Gly Ser Lys Glu Glu Lys Thr Ala Phe Thr Val Met Gln Trp Ile Val
                  85                 90                 95

Phe Ala Val Cys Ile Ile Ser Leu Leu Phe Tyr Ala Tyr Gln Thr Trp
              100                105                110

Arg Ala Thr Cys Gly Trp Glu Glu Val Tyr Val Thr Ile Ile Glu Leu
              115                120                125

Val His Val Cys Phe Gly Leu Trp His Glu Val Asp Ser Pro Cys Thr
          130                135                140

Leu Tyr Leu Ser Thr Gly Asn Met Val Leu Trp Leu Arg Tyr Ala Glu
145                150                155                160

Trp Leu Leu Thr Ser Pro Val Ile Leu Ile His Leu Ser Asn Leu Thr
                  165                170                175

Gly Met Lys Asn Asp Tyr Asn Lys Arg Thr Met Ala Leu Leu Val Ser
                  180                185                190

Asp Val Gly Cys Ile Val Trp Gly Thr Thr Ala Ala Leu Ser Thr Asp
              195                200                205

Phe Val Lys Ile Ile Phe Phe Phe Leu Gly Leu Leu Tyr Gly Phe Tyr
      210                215                220

Thr Phe Tyr Ala Ala Ala Lys Ile Tyr Ile Glu Ala Tyr His Thr Val
225                230                235                240

Pro Lys Gly Ile Cys Arg Gln Leu Val Arg Leu Gln Ala Tyr Asp Phe
                  245                250                255

Phe Phe Thr Trp Ser Met Phe Pro Ile Leu Phe Met Val Gly Pro Glu
              260                265                270

Gly Phe Gly Lys Ile Thr Ala Tyr Ser Ser Gly Ile Ala His Glu Val
          275                280                285

Cys Asp Leu Leu Ser Lys Asn Leu Trp Gly Leu Met Gly His Phe Ile
      290                295                300

Arg Val Lys Ile His Glu His Ile Leu Val His Gly Asn Ile Thr Lys
305                310                315                320

Lys Thr Lys Val Asn Val Ala Gly Asp Met Val Glu Leu Asp Thr Tyr
                  325                330                335

Val Asp Gln Asp Glu His Asp Glu Gly
              340                345

<210> SEQ ID NO 18
<211> LENGTH: 346
<212> TYPE: PRT
<213> ORGANISM: Artificial Sequence
<220> FEATURE:
<223> OTHER INFORMATION: Synthetic polypeptide

<400> SEQUENCE: 18

Met Ser Arg Leu Val Ala Ala Ser Trp Leu Leu Ala Leu Leu Leu Cys
1               5                  10                 15

Gly Ile Thr Ser Thr Thr Thr Ala Ser Ser Ala Pro Ala Ala Ser Ser
```

```
                    20                  25                  30
Thr Asp Gly Thr Ala Ala Ala Val Ser His Tyr Ala Met Asn Gly
            35                  40                  45
Phe Asp Glu Leu Ala Lys Gly Ala Val Val Pro Glu Asp His Phe Val
50                  55                  60
Cys Gly Pro Ala Asp Lys Cys Tyr Cys Ser Ala Trp Leu His Ser His
65                  70                  75                  80
Gly Ser Lys Glu Glu Lys Thr Ala Phe Thr Val Met Gln Trp Ile Val
                    85                  90                  95
Phe Ala Val Cys Ile Ile Ser Leu Leu Phe Tyr Ala Tyr Gln Thr Trp
                100                 105                 110
Arg Ala Thr Cys Gly Trp Glu Glu Val Tyr Val Thr Ile Ile Glu Leu
            115                 120                 125
Val His Val Cys Phe Gly Leu Trp His Glu Val Asp Ser Pro Cys Thr
    130                 135                 140
Leu Tyr Leu Ser Thr Gly Asn Met Val Leu Trp Leu Arg Tyr Ala Glu
145                 150                 155                 160
Trp Leu Leu Thr Ser Pro Val Ile Leu Ile His Leu Ser Asn Leu Thr
                165                 170                 175
Gly Met Lys Asn Asp Tyr Asn Lys Arg Thr Met Ala Leu Leu Val Ser
                180                 185                 190
Ala Val Gly Cys Ile Val Trp Gly Thr Thr Ala Ala Leu Ser Thr Asp
            195                 200                 205
Phe Val Lys Ile Ile Phe Phe Phe Leu Gly Leu Leu Tyr Gly Phe Tyr
    210                 215                 220
Thr Phe Tyr Ala Ala Ala Lys Ile Tyr Ile Glu Ala Tyr His Thr Val
225                 230                 235                 240
Pro Lys Gly Ile Cys Arg Gln Leu Val Arg Leu Gln Ala Tyr Asp Phe
                245                 250                 255
Phe Phe Thr Trp Ser Met Phe Pro Ile Leu Phe Met Val Gly Pro Glu
                260                 265                 270
Gly Phe Gly Lys Ile Thr Ala Tyr Ser Ser Gly Ile Ala His Glu Val
            275                 280                 285
Cys Asp Leu Leu Ser Lys Asn Leu Trp Gly Leu Met Gly His Phe Ile
    290                 295                 300
Arg Val Lys Ile His Glu His Ile Leu Val His Gly Asn Ile Thr Lys
305                 310                 315                 320
Lys Thr Lys Val Asn Val Ala Gly Asp Met Val Glu Leu Asp Thr Tyr
                325                 330                 335
Val Asp Gln Asp Glu Glu His Asp Glu Gly
                340                 345

<210> SEQ ID NO 19
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 19

Asn Lys Thr Val Trp Leu Arg Tyr Ala Glu Trp Leu Leu Thr Cys Pro
1               5                   10                  15

Val Ile Leu Ile His Leu Ser
            20
```

```
<210> SEQ ID NO 20
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 20

His Arg Val Gln Trp Leu Arg Tyr Ala Glu Trp Leu Leu Thr Cys Pro
1               5                   10                  15

Val Ile Leu Ile His Leu Ser
            20

<210> SEQ ID NO 21
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 21

Asn Gly Val Val Trp Met Arg Tyr Gly Glu Trp Leu Leu Thr Cys Pro
1               5                   10                  15

Val Leu Leu Ile His Leu Ser
            20

<210> SEQ ID NO 22
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 22

Asn Arg Val Leu Trp Leu Arg Tyr Gly Glu Trp Leu Leu Thr Cys Pro
1               5                   10                  15

Val Ile Leu Ile His Leu Ser
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 23

Asn Pro Ile Tyr Trp Ala Arg Tyr Ala Asp Trp Leu Phe Thr Thr Pro
1               5                   10                  15

Leu Thr Leu Leu Asp Leu Ala
            20

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
ttctgctacg agaatgaagt g                                          21

<210> SEQ ID NO 25
<211> LENGTH: 7
<212> TYPE: PRT
```

<213> ORGANISM: Artificial Sequence
<220> FEATURE:
<223> OTHER INFORMATION: Synthetic polypeptide

<400> SEQUENCE: 25

Phe Cys Tyr Glu Asn Glu Val
1               5

<210> SEQ ID NO 26
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 26
aaatccagaa ttacttctga aggggagtat atccctctgg atcaaataga catcaatgtt    60

<210> SEQ ID NO 27
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 27

Lys Ser Arg Ile Thr Ser Glu Gly Glu Tyr Ile Pro Leu Asp Gln Ile
1               5                   10                  15

Asp Ile Asn Val
            20

<210> SEQ ID NO 28
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 28
atggtcccgt gcacgctgct cctgctgttg gcagccgccc tggctccgac tcagacgcgg    60
gcc                                                                  63

<210> SEQ ID NO 29
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 29

Met Val Pro Cys Thr Leu Leu Leu Leu Ala Ala Ala Leu Ala Pro
1               5                   10                  15

Thr Gln Thr Arg Ala
            20

<210> SEQ ID NO 30
<211> LENGTH: 480
<212> TYPE: DNA
<213> ORGANISM: Artificial Sequence
<220> FEATURE:
<223> OTHER INFORMATION: Synthetic oligonucleotide

<400> SEQUENCE: 30
ctagactgca gagggccctg cgtatgagtg caagtgggtt ttaggaccag gatgaggcgg    60

```
ggtgggggtg cctacctgac gaccgacccc gacccactgg acaagcaccc aaccccatt       120 ccccaaattg cgcatcccct atcagagagg gggaggggaa acaggatgcg gcgaggcgcg       180
tgcgcactgc cagcttcagc accgcggaca gtgccttcgc ccccgcctgg cggcgcgcgc       240
caccgccgcc tcagcactga aggcgcgctg acgtcactcg ccggtccccc gcaaactccc       300
cttcccggcc accttggtcg cgtccgcgcc gccgccggcc cagccggacc gcaccacgcg       360
aggcgcgaga tagggggggca cgggcgcgac catctgcgct gcggcgccgg cgactcagcg       420
ctgcctcagt ctgcggtggg cagcggagga gtcgtgtcgt gcctgagagc gcagtcgaga       480

<210> SEQ ID NO 31
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 31
tacccatacg atgttccaga ttacgct                                           27

<210> SEQ ID NO 32
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 32

Tyr Pro Tyr Asp Val Pro Asp Tyr Ala
1               5
```